United States Patent
Bond et al.

(10) Patent No.: US 10,618,952 B2
(45) Date of Patent: Apr. 14, 2020

(54) PREVENTION OF N-TERMINAL TRUNCATION IN IGG LIGHT CHAINS

(71) Applicant: MEDIMMUNE LIMITED, Cambridge (GB)

(72) Inventors: Nicholas J. Bond, Cambridge (GB); Suzanne J. Gibson, Cambridge (GB); Diane Hatton, Cambridge (GB); Daniel R. Higazi, Cambridge (GB); Sarah Milne, Cambridge (GB); Mariana Alessia Sheriff, Cambridge (GB)

(73) Assignee: MedImmune Limited, Cambridge (GB)

( * ) Notice: Subject to any disclaimer, the term of this patent is extended or adjusted under 35 U.S.C. 154(b) by 0 days.

(21) Appl. No.: 15/771,906

(22) PCT Filed: Oct. 28, 2016

(86) PCT No.: PCT/EP2016/076108
§ 371 (c)(1),
(2) Date: Apr. 27, 2018

(87) PCT Pub. No.: WO2017/072310
PCT Pub. Date: May 4, 2017

(65) Prior Publication Data
US 2018/0251525 A1    Sep. 6, 2018

Related U.S. Application Data

(60) Provisional application No. 62/248,566, filed on Oct. 30, 2015.

(51) Int. Cl.
*C07K 16/00* (2006.01)
*G01N 33/68* (2006.01)
*C07K 16/18* (2006.01)

(52) U.S. Cl.
CPC .............. *C07K 16/00* (2013.01); *C07K 16/18* (2013.01); *C07K 2317/515* (2013.01); *C07K 2317/94* (2013.01); *C07K 2319/02* (2013.01)

(58) Field of Classification Search
CPC .... C07K 16/00; C07K 16/18; C07K 2319/02; C07K 2317/515; C07K 2317/94; G01N 33/6824; G01N 33/6848; G01N 33/6854; G01N 33/6857
See application file for complete search history.

(56) References Cited

FOREIGN PATENT DOCUMENTS

WO    WO-2014/060444 A1    4/2014

OTHER PUBLICATIONS

Gibson et al., Biotechnology and Bioengineering 114(9): 1970-1977 (Year: 2017).*
Ambrogelly et al., "Characterization of antibody variants during process development: The tale of incomplete processing of N-terminal secretion peptide," mAbs, vol. 4(6): 701-709 (2012).
Folz et al., "Substrate Specificity of Eukaryotic Signal Peptidase," The Journal of Biological Chemistry, vol. 263(4): 2070-2078 (1988).
Khawli et al., "Charge variants in IgG1: Isolation, characterization, in vitro binding properties and pharmacokinetics in rats," mAbs, vol. 2(6): 613-624 (2010).
Kotia et al., "Analysis of monoclonal antibody product heterogeneity resulting from alternate cleavage sites of signal peptide," Analytical Biochemistry, vol. 399: 190-195 (2010).
Nothwehr et al., "Eukaryotic Signal Peptide Structure/Function Relationships," The Journal of Biological Chemistry, vol. 264(7): 3979-3987 (1989).
Nothwehr et al., "Residues Flanking the COOH-terminal C-region of a Model Eukaryotic Signal Peptide Influence the Site of Its Cleavage by Signal Peptidase and the Extent of Coupling of Its Co-translational Translocation and Proteolytic Processing in Vitro," The Journal of Biological Chemistry, vol. 265(35): 21797-21803 (1990).
Orlandi et al., "Cloning immunoglobulin variable domains for expression by the polymerase chain reaction," Proceedings of the National Academy of Sciences U.S.A., vol. 86: 3833-3837 (1989).
Persic et al., "An integrated vector system for the eukaryotic expression of antibodies or their fragments after selection from phage display libraries," Gene, vol. 187: 9-18 (1997).
Shaw et al., "A spontaneous variant of an antidigoxin hybridoma antibody with increased affinity arises from a heavy chain signal peptide mutation," Molecular Immunology, vol. 29(4): 525-529 (1992).
Ying et al., "Identification of an alternative signal peptide cleavage site of mouse monoclonal antibodies by mass spectrometry," Immunology Letters, vol. 111: 66-68 (2007).

* cited by examiner

*Primary Examiner* — Phuong Huynh
(74) *Attorney, Agent, or Firm* — White & Case LLP

(57) ABSTRACT

We discovered that recombinant antibody light chains having a murine secretory leader sequence and an SYE motif at the N-terminus are truncated during post-translational processing. This disclosure provides two protein engineering solutions: to alter the SYE amino acid sequence of the Lc N-terminus to other alternatives; or to change the secretory leader peptide sequence. We have shown that both of these solutions are effective for preventing N-terminal light chain truncation.

22 Claims, 13 Drawing Sheets
Specification includes a Sequence Listing.

A. Intact N-term tryptic peptide: SYELTQPPSVSVSPGQTASITCSGHNLEDK (SEQ ID NO: 20)
B. Truncated N-term tryptic peptide: LTQPPSVSVSPGQTASITCSGHNLEDK (SEQ ID NO: 21)

Figure 11

*SVEL*TQPPSVSVSVSPGQTASITCSGHNLEDKFASWYQQKPGQSPVLVIYRDDKRPSGIPERFSASNSGHTATLTISG TQAMDEADYYCQAQDSTTRVFGGGTKLTVLGQPKAAPSVTLFPPSSEELQANKATLVCLISDFYPGAVTVAW KADSSPVKAGVETTTPSKQSNNKYAASSYLSLTPEQWKSHRSYSCQVTHEGSTVEKTVAPTECS

PREVENTION OF N-TERMINAL TRUNCATION IN IGG LIGHT CHAINS

RELATED APPLICATIONS

This application is a U.S. National Stage Application under 35 U.S.C. § 371 of International Application No. PCT/EP2016/076108, filed Oct. 28, 2016, which claims the benefit of U.S. Provisional Application No. 62/248,566, filed Oct. 30, 2015. The specifications of each of the foregoing applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Apr. 27, 2018, is named 1848081_002_096_301_SL and is 10,239 bytes in size.

BACKGROUND

Immunoglobulin G (IgG) antibodies consist of two heavy chains (Hc) and two light chains (Lc). Monoclonal antibodies (mAbs) have been increasingly developed as medicines over the last three decades and represent the fastest growing class of therapeutic agents (Walsh, *Biopharmaceutical Benchmarks* 2014; Reichert, *mAbs* 2:84-100, 2010). This has been enabled by the development of technologies for antibody discovery, such as phage and ribosome display and transgenic mice with human antibody repertoires (Strohl, *Curr. Drug Discov. Technol.* 11:1-2, 2014). In a biopharmaceutical environment, antibodies can be generated by molecular manipulation of DNA and transfection of mammalian host cells to produce specifically targeted biotherapeutics. The lead antibody molecules from the discovery process need to be produced in significant quantities for use in development and for clinical applications. Typically, the large scale production of recombinant antibodies employs stable recombinant mammalian cell lines such as CHO or NS0, owing to the ability of these host cells to correctly fold and assemble antibodies, and to perform the required post-translational modifications (Walsh, 2014). Generally, the host cell lines are engineered by transfecting and selecting for the integration of expression plasmids encoding the antibody genes of interest. For example, Chinese Hamster Ovary (CHO) cells can be transfected with DNA containing coding regions for Lc and Hc variable and constant domains. This DNA stably integrates into the CHO host cell genome, and is then transcribed and translated to produce the Lc and Hc polypeptides, each of which contains a secretory leader sequence.

The secretory leader sequences act as a "postcode" for the peptides, directing the nascent polypeptides from the cytosol through translocons to the endoplasmic reticulum (ER). More particularly, as the nascent polypeptide emerges from the ribosome in the cytosol, the signal peptide binds to the signal recognition particle (SRP) and this complex is targeted to the translocon in the endoplasmic reticulum (Nyathi et al., *Molec. Cell Res.* 1833:2392-2402, 2013). Then, as the polypeptide is translocated from the cytosol across the membrane into the ER, the signal peptide itself is cleaved off by the signal peptidase so that the signal peptide is not part of the mature protein. The Hc and Lc polypeptides are processed into the final antibody protein product by the cellular machinery, and the antibody is secreted into the cell supernatant.

Eukaryotic signal peptides are characterized by structural homology, rather than significant sequence conservation, having a three-domain structure: a positively charged N-terminal domain (N-domain), a central hydrophobic region (h-domain) and a more polar C-terminal region (C-domain) (Von Heijne, *J. Molec. Biol.* 184:99-105, 1985). The h-domain is a major feature for SRP recognition and binding, and the hydrophobicity is important for translocation across the ER membrane (Nilsson et al., *J. Molec. Biol.* 427:1191-1201, 2015). The C-domain defines the cleavage site and must fulfil a "−3, −1 rule" (Von Heijne, *J. Molec. Biol.* 173:243-251, 1984; Von Heijne, *Eur. J. Biochem.* 133:17-21, 1983), where the −1 position of the signal peptide (i.e., the last residue before the cleavage site) must be occupied by A/S/G/C/T/Q amino acid residues, and must not have aromatic (F/H/W), charged (D/Q/K/R), or large polar residues (N/Q) in position −3, as well as no P from −3 to +1. A similar signal peptidase recognition site, A-X-B, just before the cleavage site, has also been postulated (Perlman et al., *J. Molec. Biol.* 167:391-409, 1983). Position A consists of A/G/S residues or the larger aliphatic amino acids L/V/I, and position B is occupied by A/G/S. The amino acid occupying −1 of the signal peptide is critical for the site of signal peptidase cleavage (Folz et al., *J. Biol. Chem.* 263:2070-2078, 1988). In addition, the identity of amino acid residues upstream of the −1 and −3 positions and the h-/C-domain junction influences the site and efficiency of cleavage (Nothwehr et al., *J. Biol. Chem.* 264:3979-3987, 1989). The position of the junction between the N- and h-domains also influences the cleavage site (Nothwehr et al., *J. Biol. Chem.* 265:21797-21803, 1990).

It is essential that therapeutic antibodies are produced consistently; transfected cell lines must produce protein that is stable and has reproducible product quality attributes. For instance, it is undesirable to have impurities (i.e., any substance that is not part of the final, intact monoclonal antibody or final formulation buffer) in the final therapeutic protein product. Impurities can lead to instability of the product, and they have the potential to cause immunogenicity, decrease the potency of the product and/or have off-target effects, which could compromise patient safety. Impurities can be removed by downstream processing of the raw cell culture harvest; however, this process is expensive in both time and cost of goods. Therefore, it is beneficial to ensure there are as few impurities present in the final culture harvest as possible before downstream processing. It is also difficult to both detect and remove impurities that closely resemble the IgG product. As such, it is desirable for these product-related variants to be minimized in the culture harvest.

The signal peptide cleavage process is generally highly efficient for antibodies, producing a high proportion of correctly cleaved heavy and light chain polypeptides. However, there are some documented cases where the cleavage site is variable resulting in truncation or extension of mAb heavy and light chains (Ambrogelly et al., mAbs 4:701-709, 2012; Kotia et al., *Anal. Biochem.* 399:190-195, 2010; Ying et al., *Immunol. Lett.* 111:66-68, 2007; Shaw et al., *Molec. Immunol.* 29:525-529, 1992). We have used the murine heavy chain signal peptide sequence (Persic et al., *Gene* 187:9-18, 1997; Orlandi et al., *Proc. Natl. Acad. Sci. USA* 86:3833-3837, 1989) for secretion of heavy and light chains for a wide variety of human antibodies and have observed correct processing of the signal peptide resulting in a highly homogeneous N-terminal sequence. Here we describe the characterization and prevention of a recombinant human IgG light chain truncation, not previously detailed in the literature, that is associated with the combination of a murine heavy chain signal peptide sequence with lambda light chains carrying an N-terminal SYE amino acid motif.

Specifically, during development of a therapeutic IgG (MEDI8490), disclosed in U.S. patent application Ser. No. 14/435,520 herein incorporated by reference in its entirety, we observed that about 3-8% of the final antibody product contained a truncated Lc peptide. The truncated Lc was missing three amino acids at its N-terminus: serine-tyrosine-glutamic acid (SYE). The truncated Lc was detected by liquid chromatography-mass spectrometry (LC-MS) analysis of deglycosylated IgG, and was confirmed by reduced peptide mapping analysis. The truncated Lc is considered to be a product-related variant. In order to increase the homogeneity of the product and to reduce product development risks, we investigated ways to prevent the Lc SYE truncate from being produced. Two different protein engineering solutions were explored: (1) alteration of the Lc N-terminal SYE amino acid sequence to other alternatives; (2) changes to the secretory leader peptide sequence. We have shown that both of these solutions are effective for preventing N-terminal Lc truncation in the MEDI8490 antibody and other IgG proteins. This demonstrates that these are broadly applicable solutions to this issue for IgG production.

BRIEF SUMMARY OF THE INVENTION

Some of the main aspects of the present invention are summarized below. Additional aspects are described in the Detailed Description of the Invention, Examples, Drawings, and Claims sections of this disclosure. The description in each section of this disclosure is intended to be read in conjunction with the other sections. Furthermore, the various embodiments described in each section of this disclosure can be combined in various different ways, and all such combinations are intended to fall within the scope of the present invention.

In one aspect, we provide a method of producing an untruncated mature antibody Lc polypeptide comprising: (a) identifying a first antibody Lc amino acid sequence comprising a first nascent N-terminal sequence shown in SEQ ID NO: 5 [murine leader+Ser-Tyr-Glu]; and (b) expressing in a cultured cell a second antibody Lc polypeptide having the same amino acid sequence as the first antibody Lc polypeptide, except that instead of the first nascent N-terminal sequence, the second antibody Lc polypeptide comprises a second nascent N-terminal sequence selected from the group consisting of SEQ ID NO: 6 [murine leader+Ser-Ser-Glu], SEQ ID NO: 7 [murine leader+Ser-Tyr-Val], SEQ ID NO: 8 [murine leader+Gln-Ser-Val], SEQ ID NO: 9 [murine leader+Gln-Ala-Val], SEQ ID NO: 10 [murine leader+Gln-Ser-Ala], SEQ ID NO: 11 [murine leader+Gln-Tyr-Val], SEQ ID NO: 12 [V-lambda 3 leader+Ser-Tyr-Glu], SEQ ID NO: 13 [V-lambda 1 leader+Ser-Tyr-Glu], and SEQ ID NO: 14 [V-kappa 1 leader+Ser-Tyr-Glu]; thereby producing an untruncated mature antibody Lc polypeptide that does not truncate the first three amino acids (SYE).

In another aspect, we provide a method of preventing N-terminal truncation of an antibody Lc polypeptide, the method comprising: (a) identifying a first antibody Lc polypeptide having an amino acid sequence comprising a first nascent N-terminal sequence shown in SEQ ID NO: 5 [murine leader+Ser-Tyr-Glu], wherein the first nascent N-terminal sequence consists essentially of a leader sequence and a mature N-terminal tripeptide, wherein expression of the first antibody Lc polypeptide in a cultured cell results in truncation of the mature N-terminal tripeptide in at least approximately 3% of first antibody Lc polypeptides expressed in the cultured cell; and (b) expressing in a cultured cell a second antibody Lc polypeptide having the same amino acid sequence as the first antibody Lc polypeptide, except that instead of the first nascent N-terminal sequence, the second antibody Lc polypeptide comprises a second nascent N-terminal sequence selected from the group consisting of SEQ ID NO: 6 [murine leader+Ser-Ser-Glu], SEQ ID NO: 7 [murine leader+Ser-Tyr-Val], SEQ ID NO: 8 [murine leader+Gln-Ser-Val], SEQ ID NO: 9 [murine leader+Gln-Ala-Val], SEQ ID NO: 10 [murine leader+Gln-Ser-Ala], SEQ ID NO: 11 [murine leader+Gln-Tyr-Val], SEQ ID NO: 12 [V-lambda 3 leader+Ser-Tyr-Glu], SEQ ID NO: 13 [V-lambda 1 leader+Ser-Tyr-Glu], and SEQ ID NO: 14 [V-kappa 1 leader+Ser-Tyr-Glu]; wherein the second nascent N-terminal sequence consists essentially of a leader sequence and a mature N-terminal tripeptide; and wherein expression of the second antibody Lc polypeptide in the cultured cell results in no truncation of the mature N-terminal tripeptide; thereby preventing N-terminal truncation of an antibody Lc polypeptide.

In a further aspect, we provide a method of producing a composition comprising a homogenous population of antibody Lc polypeptides, the method comprising: (a) identifying a first Lc polypeptide having an amino acid sequence comprising a first nascent N-terminal sequence shown in SEQ ID NO: 5 [murine leader+Ser-Tyr-Glu]; (b) expressing in a cultured cell a second Lc polypeptide, wherein the second Lc polypeptide has the same amino acid sequence as the first Lc polypeptide, except that the second Lc polypeptide comprises a second nascent N-terminal sequence selected from the group consisting of SEQ ID NO: 6 [murine leader+Ser-Ser-Glu], SEQ ID NO: 7 [murine leader+Ser-Tyr-Val], SEQ ID NO: 8 [murine leader+Gln-Ser-Val], SEQ ID NO: 9 [murine leader+Gln-Ala-Val], SEQ ID NO: 10 [murine leader+Gln-Ser-Ala], SEQ ID NO: 11 [murine leader+Gln-Tyr-Val], SEQ ID NO: 12 [V-lambda 3 leader+Ser-Tyr-Glu], SEQ ID NO: 13 [V-lambda 1 leader+Ser-Tyr-Glu], and SEQ ID NO: 14 [V-kappa 1 leader+Ser-Tyr-Glu]; wherein the second Lc polypeptide is secreted into supernatant by the cultured cell, wherein the supernatant is at least 98% free of amino acid sequence variants of the second Lc polypeptide; and (c) harvesting the second Lc polypeptide from the supernatant; thereby producing a composition comprising a homogenous population of antibody Lc polypeptides. Preferably, the composition is a pharmaceutical composition. In some embodiments, the first Lc polypeptide and/or the second Lc polypeptide is part of an antibody. Preferably, the antibody is a therapeutic antibody. Preferably, the supernatant is at least 99%, or 100% free of amino acid sequence variants of the second Lc polypeptide. Amino acid sequence variants can be detected using reverse phase liquid chromatography-mass spectrometry (LC-MS).

The cultured cell is a eukaryotic animal cell, preferably a mammalian cell. In some instances, the cultured cell is a CHO cell.

In some instances, the second nascent N-terminal sequence is SEQ ID NO: 6. In some instances, the second nascent N-terminal sequence is SEQ ID NO: 7. In some instances, the second nascent N-terminal sequence is SEQ ID NO: 8. In some instances, the second nascent N-terminal sequence is SEQ ID NO: 9. In some instances, the second nascent N-terminal sequence is SEQ ID NO: 10. In some instances, the second nascent N-terminal sequence is SEQ ID NO: 11. In some instances, the second nascent N-terminal sequence is SEQ ID NO: 12. In some instances, the second nascent N-terminal sequence is SEQ ID NO: 13. In some instances, the second nascent N-terminal sequence is SEQ ID NO: 14.

BRIEF DESCRIPTION OF THE DRAWINGS/FIGURES

FIG. 1A shows deconvoluted mass spectrometry analysis of a MEDI8490 Lc produced from an expression construct encoding the SYE Lc and the murine Hc leader sequence (SEQ ID NO: 5). In addition to the main peak (22,692 Da), which was consistent with the untruncated Lc, a species of 22,313 Da was detected, which was consistent with the theoretical molecular weight of a truncated Lc species. FIG. 1B shows peptide mapping analysis of transiently expressed CHO material, and confirms that the truncate is missing the first three N-terminal amino acids (SYE).

FIG. 1C schematically shows the first 22 N-terminal amino acids N-terminus of the MEDCI8490 Lc (top sequence in black; SEQ ID NO: 15) with the correct and alternative cleavage sites (↓) of the murine signal peptide (top sequence in grey; SEQ ID NO: 1), and the first 19 N-terminal amino acids of the SYE truncate (middle sequence; SEQ ID NO: 22) and first 22 N-terminal amino acids of the fill length truncate (bottom sequence; SEQ ID NO: 21).

FIG. 2A shows the relative proportion (%) of truncated Lc (black bars) and full-length Lc (grey bars) for MEDI8490 produced from different bioreactor scales and expression platforms. Transient expression in 5 L scale, stable expression in 50 L and 250 L scale of two independent primary transfectants is shown. FIG. 2B shows MEDI8490 produced from seven clones from six independent stable transfectant lineages at 5 L bioreactor scale. The relative proportion (%) of truncated Lc (black bars) and full-length Lc (gray bars) was determined by LC-MS analysis of reduced IgG.

Figure 10A:
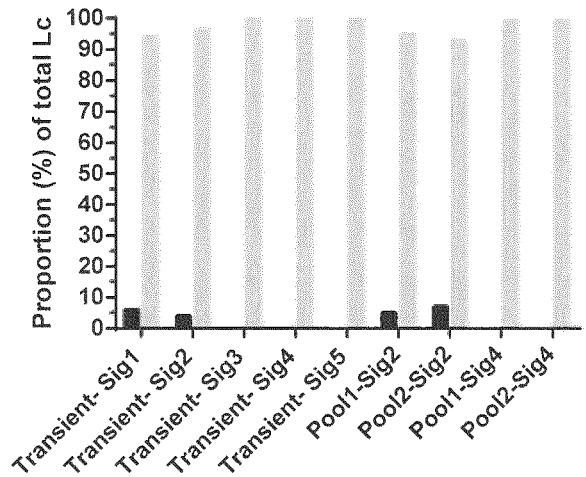
Figure 10B:
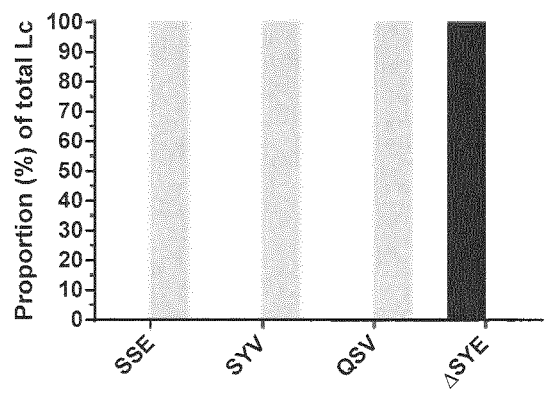
Figure 10C:
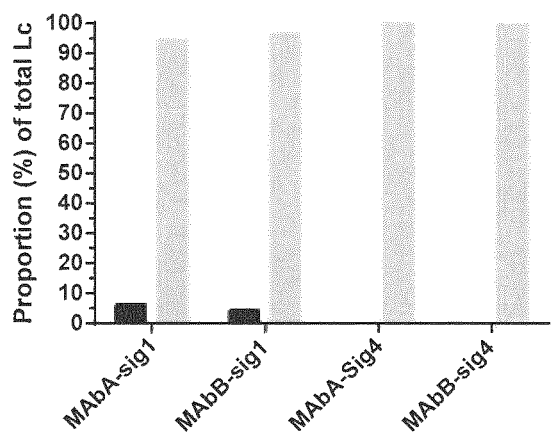

FIG. 10A shows the relative proportion (%) of truncated (black bars) and full-length (grey bars) Lc for MEDI8490 produced by transient and stable expression systems using different signal peptides (listed in Table 5). FIG. 10B shows the relative proportion (%) of truncated (black bars) and full-length (grey bars) Lc for MEDI8490 using different Lc N-terminal amino acid sequences. FIG. 10C shows the relative proportion (%) of truncated (black bars) and full-length (grey bars) Lc for two unrelated mAbs (A and B) with SYE N-termini with either the murine (Sig 1; SEQ ID NO: 1)) or an alternative (Sig 4; SEQ ID NO: 3)) signal peptide. The relative proportions of truncated and full-length Lc were determined by LC-MS analysis of the reduced IgG.

FIG. 11 shows the amino acid sequence of the MEDI8490 SYE Lc (SEQ ID NO: 15). The N-terminal SYE motif is underlined. The SYE motif is replaced by Ser-Ser-Glu in the SSE Lc, by Ser-Tyr-Val in the SYV Lc, by Gln-Ser-Val in the QSV Lc, by Gln-Ala-Val in the QAV Lc, by Gln-Ser-Ala in the QSA Lc, and by Gln-Tyr-Val in the QYV Lc.

DETAILED DESCRIPTION OF THE INVENTION

The invention provides methods for preventing N-terminal truncation of Lc polypeptides. At early stages of therapeutic mAb development, quality-related attributes of the molecule are evaluated during routine assessments to ensure suitability for development and manufacture. During such developability assessments, a truncated light chain variant of MEDI8490, a recombinant human IgG1, was observed by LC-MS analysis of the reduced IgG. LC-MS and peptide mapping analysis revealed that the first three amino acids (SYE) from the N-terminus of the mature light chain were truncated in approximately 3-8% of the molecules, and consistently present in product from transient and stable expression platforms and from different bioreactor scales and CHO cell lineages. It has been demonstrated that the amino acids flanking the C-terminus of the signal peptide can influence the cleavage site (Nothwehr et al., 1990; Nothwehr et al., 1989; Folz et al., 1988).

The original leader sequence that gave rise to the truncated Lc had the amino acid sequence MGWSCIILFL-VATATGVHS (SEQ ID NO: 1). This is a murine heavy chain leader, which is often used for recombinant mAb production (Persic et al., 1997). The murine signal peptide conforms with the '−3, −1' and 'A-X-B' rules for cleavage site (Von Heijne 1983, 1984; Perlman and Halvorson, 1983), having V at −3 or A and S at −1 or B, respectively. The Lc truncation is specific to molecules having the SYE motif at the N-terminus (SYE Lc). This discovery was unexpected; the murine Hc leader sequence is widely used in the production of human Hc and Lc polypeptides for a broad range of therapeutic IgG molecules, and no truncation issues have been observed previously.

The presence of truncated polypeptide is a disadvantage, creating a variable amount of product-related variant that requires extra downstream processing to remove and thereby reducing product yield. In addition, for some antibodies, truncation of the Hc at the N-terminus has been reported to affect binding specificity (Shaw et al., 1992). The truncation in the MEDI8490 Lc did not affect potency. However, the MEDI8490 product-related variant was undesirable due to potential batch-to-batch variation of product quality attributes (Ambrogelly et al., 2012; Kotia et al., 2010; Ying et al., 2007). The preferred strategy was to prevent the truncation of the MEDI8490 Lc protein at source, i.e. in the cell culture process, rather than control or remove it during purification.

We therefore investigated the use of alternative V-lambda 3 germlined Lc N-termini and also three alternative signal peptides as two approaches to avoid the occurrence of this truncation.

We found that by changing the secretory leader peptide sequence at the N-terminus of the Lc, we could prevent occurrence of this truncation. We replaced the standard murine leader sequence with three different leader sequences: two leader sequences from the V-lambda family, MAWTPLLLPLLTFCTSEA (SEQ ID NO: 2) and MAGFPLLLTLLTHCAGSWA (SEQ ID NO: 3), and the kappa Lc leader sequence, MDMRVPAQLLGLLLLWLPGAKC (SEQ ID NO: 4). The SYE truncation did not occur with these alternate leader sequences, and we achieved 100% desired product in each case. We have applied this method for avoiding light chain truncates to other IgG light chains that have the SYE N-terminal sequence, and no Lc truncate has been detected for these molecules, demonstrating that this solution is a generally applicable and not specific to the original MEDI8490 molecule.

It is also possible to prevent the truncation by retaining the standard murine leader sequence and altering the first three amino acids of the Lc N-terminus, for example, to SYV, SSE, QSV, QAV, QSA, or QYV. Moreover, the person of skill in the art will appreciate that other three amino acid start sequences commonly used in the art that are not SYE are contemplated by the present invention. Further, additional sequences can be developed using this method by selecting three amino acid sequences that would not significantly alter the molecule's characteristics, e.g., specificity, target-binding, and/or product stability, are not affected by the change in amino acid sequence.

In other words, we provide broadly applicable methods of preventing N-terminal Lc truncation and producing an untruncated, i.e. full-length, mature antibody Lc by replacing the nascent N-terminal Lc sequence comprising SEQ ID NO: 5 with a nascent N-terminal Lc sequence comprising any one of SEQ ID NOs: 6-14. We also provide methods of producing a composition comprising a homogenous population of antibody molecules by replacing the nascent N-terminal Lc sequence comprising SEQ ID NO: 5 with a nascent N-terminal Lc sequence comprising any one of SEQ ID NOs: 6-14, expressing the Lc polypeptide comprising the replaced nascent sequence in a cultured cell, and harvesting the Lc polypeptide from the cell culture supernatant, all of which can be accomplished using methods known to a person of ordinary skill in the art. In embodiments where antibodies are produced, antibody heavy chains are also expressed in the cultured cells.

As a result of this work, the 'SYE' Lc N-terminal sequence has been identified as a sequence liability for development of IgG molecules. If the 'SYE' can be altered without causing detrimental effects to the molecule during the lead isolation and optimization steps, it is altered. If this is not possible, an alternative leader sequence (e.g. a V-lambda 1 family leader sequence) is used, rather than the murine Hc leader sequence, when the 'SYE' N-terminal Lc motif appears. As a result, Lc truncation is prevented.

As used in this specification and the appended claims, the singular forms "a," "an," and "the" include plural referents, unless the context clearly dictates otherwise. The terms "a" (or "an") as well as the terms "one or more" and "at least one" can be used interchangeably.

Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Unless defined otherwise, all technical and scientific terms used herein have the same meaning as commonly understood by one of ordinary skill in the art to which this invention is related. For example, *The Dictionary of Cell and Molecular Biology* (5th ed. J. M. Lackie ed., 2013), the *Oxford Dictionary of Biochemistry and Molecular Biology* (2d ed. R. Cammack et al. eds., 2008), and *The Concise Dictionary of Biomedicine and Molecular Biology* (2d ed. P-S. Juo, 2002) can provide one of skill with general definitions of some terms used herein.

Units, prefixes and symbols are denoted in their Système International de Unites (SI) accepted form. Numeric ranges are inclusive of the numbers defining the range. The headings provided herein are not limitations of the various aspects or embodiments of the invention, which can be had by reference to the specification as a whole. Accordingly, the terms defined immediately below are more fully defined by reference to the specification in its entirety.

Wherever embodiments are described with the language "comprising," otherwise analogous embodiments described in terms of "consisting of" and/or "consisting essentially of" are included.

Amino acids are referred to herein by their commonly known three-letter symbols or by the one-letter symbols recommended by the IUPAC-IUB Biochemical Nomenclature Commission. Nucleotides, likewise, are referred to by their commonly accepted single-letter codes.

The terms "antibody" or "immunoglobulin" are used interchangeably herein. A typical antibody comprises at least two heavy (H) chains and two light (L) chains interconnected by disulfide bonds. Each heavy chain is comprised of a heavy chain variable region (abbreviated herein as VH) and a heavy chain constant region. The heavy chain constant region is comprised of three domains, CH1, CH2, and CH3. Each light chain is comprised of a light chain variable region (abbreviated herein as VL) and a light chain constant region (CL). The light chain constant region is comprised of one domain, Cl. The VH and VL regions can be further subdivided into regions of hypervariability, termed Complementarity Determining Regions (CDR), interspersed with regions that are more conserved, termed framework (FW) regions. Each VH and VL is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain that interacts with an antigen. The constant regions of the antibodies can mediate the binding of the immunoglobulin to host tissues or factors, including various cells of the immune system (e.g. effector cells) and the first component (C1q) of the classical complement system.

The term "antibody" can refer to an immunoglobulin molecule that recognizes and specifically binds to a target, such as a protein, polypeptide, peptide, carbohydrate, polynucleotide, lipid or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2 and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody and any other modified immunoglobulin molecule comprising an antigen recognition site so long as the antibodies exhibit the desired biological activity. An antibody can be of any the five major classes of immunoglobulins: IgA, IgD, IgE, IgG and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma and mu respectively. The different classes of immunoglobulins have different and well-known subunit structures and three-dimensional configurations. There are two classes of mammalian light chains, lambda and kappa. Antibodies can be naked or conjugated to other molecules such as toxins, radioisotopes, etc.

The terms "polypeptide", "peptide" and "protein" are used interchangeably herein to refer to polymers of amino acids of any length. The polymer can be linear or branched, it can comprise modified amino acids and non-amino acids can interrupt it. The terms also encompass an amino acid polymer that has been modified naturally or by intervention; for example, disulfide bond formation, glycosylation, lipidation, acetylation, phosphorylation or any other manipulation or modification such as conjugation with a labeling component. Also included within the definition are, for example, polypeptides containing one or more analogs of an amino acid (including, for example, unnatural amino acids, etc.), as well as other modifications known in the art. In certain embodiments, the polypeptides can occur as single chains or associated chains.

A "leader sequence" is a short peptide (typically about 5-30 amino acids long) that is present at the N-terminus of newly synthesized polypeptides that will be transported across cellular membranes. The leader sequence directs the polypeptide to the endoplasmic reticulum (ER) through protein-conducting channels called translocons. The leader sequence is cleaved from the polypeptide in the ER, and does not form part of the mature protein. The leader sequence is sometimes referred to as a secretory sequence, leader peptide, secretory leader peptide, signal peptide, signal sequence, targeting signal, localization signal, localization sequence or transit peptide; these terms are used interchangeably herein.

A "mature" polypeptide or sequence (e.g. a mature antibody Lc) means one that has undergone intracellular post-translational processing to remove the secretory leader sequence. A "nascent" polypeptide or sequence (e.g. a nascent N-terminal sequence) means one in which the leader sequence has not been cleaved. An "untruncated" polypeptide is one in which the leader peptide has been cleaved, but the N-terminal amino acids of the mature polypeptide have not been cleaved during post-translational processing.

A "therapeutic antibody" is one that can be administered to a subject to treat or prevent a disease or condition. A "subject" is any individual, particularly a mammal, for whom diagnosis, prognosis, or therapy is desired. Mammalian subjects include humans, domestic animals, farm animals, sports animals and zoo animals, e.g. humans, non-human primates, dogs, cats, guinea pigs, rabbits, rats, mice, horses, cattle, etc. To "treat" refers to therapeutic measures that cure, slow down, lessen symptoms of and/or halt progression of a diagnosed pathologic condition or disorder. Thus, those in need of treatment include those already with the disorder. To "prevent" refers to prophylactic or preventative measures that prevent and/or slow the development of a targeted pathologic condition or disorder. Thus, those in need of prevention include those prone to have or susceptible to the disorder.

The term "pharmaceutical composition" refers to a preparation that is in such form as to permit the biological activity of the active ingredient to be effective and which contains no additional components that are unacceptably toxic to a subject to which the composition would be administered. Such composition can be sterile and can comprise a pharmaceutically acceptable carrier, such as physiological saline. Suitable pharmaceutical compositions can comprise one or more of a buffer (e.g. acetate, phosphate or citrate buffer), a surfactant (e.g. polysorbate), a stabilizing agent (e.g. human albumin), a preservative (e.g. benzyl alcohol), an absorption promoter to enhance bioavailability and/or other conventional solubilizing or dispersing agents.

All of the references cited in this disclosure are hereby incorporated by reference in their entireties. In addition, any manufacturers' instructions or catalogues for any products cited or mentioned herein are incorporated by reference. Documents incorporated by reference into this text, or any teachings therein, can be used in the practice of the present invention. Documents incorporated by reference into this text are not admitted to be prior art.

The invention is further described in the following non-limiting Examples.

EXAMPLES

Example 1

Materials and Methods

Expression Constructs

Plasmids were constructed for both transient and stable transfection using DNA encoding specific leader and/or altered N-terminal variable Lc regions (GeneArt®, Life Technologies, Carlsbad, Calif.). DNA was subjected to restriction digestion and ligation to assemble the required functional components into the appropriate plasmid backbones.

Plasmids were constructed using enzymatic digestion and ligation of pEU vectors for transient expression, and GS tandem vectors for stable expression. pEU vectors contain the following elements: AmpR, polyA, oriP, pUC ori, EBNA-1, EF-1 alpha promoter and appropriate Hc/Lc DNA fragments. The IgG expression plasmids used for transient transfections were based on the expression vectors described by Persic et al. (1997) and Daramola et al. (*Biotechnol. Progress* 30:132-141, 2014). The IgG expression plasmids used for stable transfections were based on the pEE12.4 expression plasmid (Lonza Group, Basel, Switzerland). GS tandem vectors contain the following elements: Beta Lactamase, SV40 and SV40 poly A, Glutamine synthetase cDNA, hCMV-MIE promoters, pEE6 ori and appropriate Hc/Lc DNA fragments.

Transient Transfection

Expression plasmids for the human mAbs MEDI8490, mAb A and mAb B (all IgG γ1™, λ; Organesyan et al., *Acta Crystallogr. D Biol. Crystallogr.* 64:700-704, 2008) were assessed by transient expression. Transient transfections were carried out according to the method described by Daramola et al. (*Biotechnol. Progress*, 30:132-141, 2014) using Hc and Lc vectors, polyethyeneimine (PEI; Polysciences, Inc., Warrington, Pa.) and CHO cells in CD-CHO medium (Life Technologies, Carlsbad, Calif.) or proprietary medium. A proprietary nutrient feed was supplemented as bolus additions over the course of the culture period.

Stable CHO Pool Transfection

Stable transfections in CHOKISV cells were performed using Amaxa® Nucleofector® system and reagents (Lonza Group, Basel, Switzerland). Transfected cells were selected and maintained in CD CHO in the presence of methionine sulfoximine (MSX). Pools of cells were expanded and then used for recombinant protein production in a 14-17 day fed batch process using CD CHO. A proprietary nutrient feed was supplemented as bolus additions over the course of the culture period.

Stable CHO Primary Transfectants and Clonal Cell Lines

Stable CHO primary transfectants were generated by transfecting CHOKISV cells, as described above for stable pools. The transfected cells were then diluted and selected in CD CHO in the presence of MSX. Individual colonies were expanded and then assessed for titer, cell density and viability in a fed-batch process, as described for pools above. Clonal cell lines were isolated from the primary transfectants by limiting dilution cloning in CD CHO in the presence of MSX in 96-well plates. Individual colonies were expanded and assessed for growth and productivity in a 14-day fed-batch process, using proprietary medium with bolus additions of a proprietary nutrient feed.

Purification and Quantitation of IgG

Cell culture supernatant was harvested by centrifugation. The clarified harvest was purified by standard Protein A affinity chromatography using MabSelect SuRe™ (GE Healthcare Life Sciences, Piscataway, N.J.). IgG in cell culture supernatants was characterized by QTOF mass spectrometry to detect the presence or absence of Lc truncation, or was quantified by Protein-A HPLC affinity chromatography on an Agilent HP1100 Series or HP1200 Series (Agilent Technologies, Santa Clara, Calif.) by comparing peak size from each sample with a calibration curve.

Mass Spectrometry: Reduced IgG Analysis

Reverse phase LC-MS analysis was performed using an ACQUITY UPLC® system coupled to a SYNAPT® G1 QTOF spectrometer (Waters Corporation, Milford, Conn.). Purified protein at 1 mg/ml was reduced by incubation at 37° C. for 30 minutes in 10 mM DTT, 10 mM Tris HCl, pH 8 and 2 μg was injected onto a 50 mm×2.1 mm BEH C4 analytical column (1.7 μm particle size), held at 65° C. (Waters Corporation, Milford, Conn.). Protein was eluted at a constant flow rate of 0.15 mL/min using a 15 minute binary gradient; Solvent B was initially held at 5% for 3 minutes, increased to 25% over the next minute, then to 45% over 10 minutes before increasing to 95% over the final minute. The column was cleaned prior to the next injection by oscillating between high (95%) and low (5%) Solvent B for 7 minutes. Solvent A (water) and Solvent B (acetonitrile) were supplemented with 0.01% (v/v) trifluoroacetic acid and 0.1% (v/v) formic acid. Spectra were acquired between 500-4500 Th. Instrument parameters included +ve ionization mode, source voltage of 3.4 kV, sample cone voltage of 50 V, source temperature of 140° C., and desolvation temperature of 400° C. Protein charge envelopes were deconvoluted using MaxEnt 1. For a given sample, quantitative assessments of the non-truncated LC and truncated species were determined by dividing the ion current detected for the SYE-truncated species by the summed detected ion current for non-truncated LC and truncated species. The proportion of truncated LC was reported in % of total LC and did not consider other LC modifications.

Mass Spectrometry: Reduced Peptide Map Analysis

For each sample, 100 μg of protein at 1.6 mg/ml was denatured and reduced in 5.2 M Guanidine, 85 mM Tris, 0.7 mM EDTA and 16 mM DTT, pH 7.6, for 30 minutes at 37° C. Following reduction, samples were incubated with 40 mM iodoacetamide in the dark, at room temperature, for 30 minutes. Reduced and alkylated protein was buffer exchanged into 2 M urea, 100 mM Tris, pH 7.6 and incubated at 37° C. for 4 hours with trypsin at an enzyme to substrate ratio of 1:20.

Protein digests were analyzed by reverse phase LC-MS using an ACQUITY UPLC® system coupled to a SYNAPT® G2 QTOF spectrometer (Waters Corporation, Milford, Conn.) mass spectrometer (Waters Corporation, Milford, Conn.). For each sample, 5 μg of Glu-C tryptic digest was injected onto a 150 mm×2.1 mm BEH300 C18 analytical column (1.7 μm particle size), held at 55° C. (Waters Corporation, Milford, Conn.). Peptides were eluted at a constant flow rate of 0.2 mL/min using a 75 minute binary gradient; Solvent B was increased from 0% to 35%. The column was cleaned prior to the subsequent injection by oscillating between high (95%) and low (5%) Solvent B for 5 minutes. Solvent A (water) and Solvent B (acetonitrile) were supplemented with 0.02% (v/v) trifluoroacetic acid. Spectra were acquired between 50-2500 m/z using a data-independent mode of acquisition. Low and high energy spectra were processed using BiopharmaLynx™ software (Waters Corporation, Milford, Conn.).

cDNA Sequence Analysis

Sequence analysis of individual MEDI8490 Lc transcripts from stably transfected CHO cell lines was performed by isolation of RNA from CHO cells using RNeasy Mini Kit (Qiagen, Germantown, Md.), followed by RT-PCR of the Lc mRNA using the Transcriptor One-Step RT-PCR Kit (Roche Diagnostics Corporation, Indianapolis, Ind.), cloning of resulting cDNAs using the Invitrogen™ TOPO®-TA cloning kit (Thermo Fisher Scientific, Inc., Waltham, Mass.) and transformation into *E. coli*, all according to the manufacturers' instructions. The cloned sequences in the resulting individual colonies were sequence verified using the Sanger method for sequencing.

Example 2

Identification of a Light Chain Truncate in the Cell Culture Harvest of Transiently Expressed MEDI8490

Figure 1A:
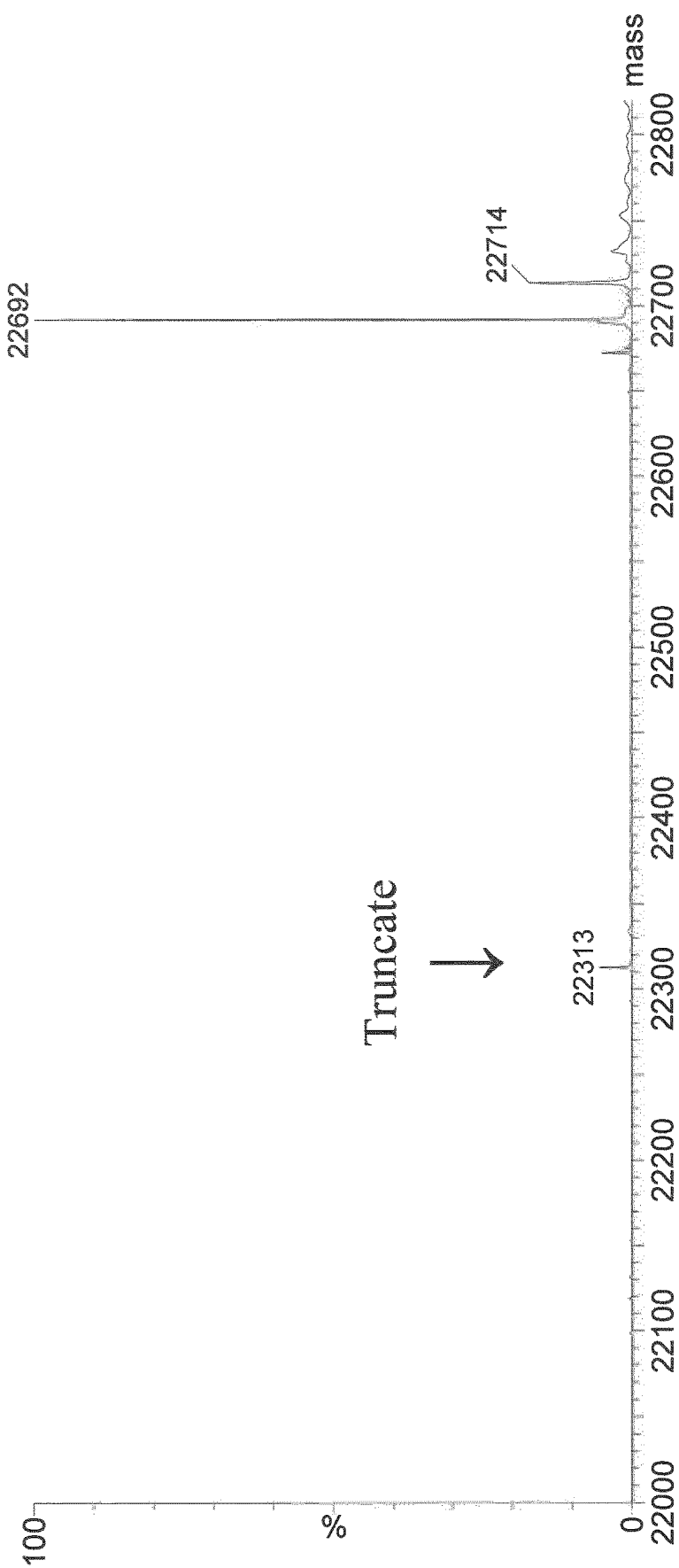
Figure 1B:
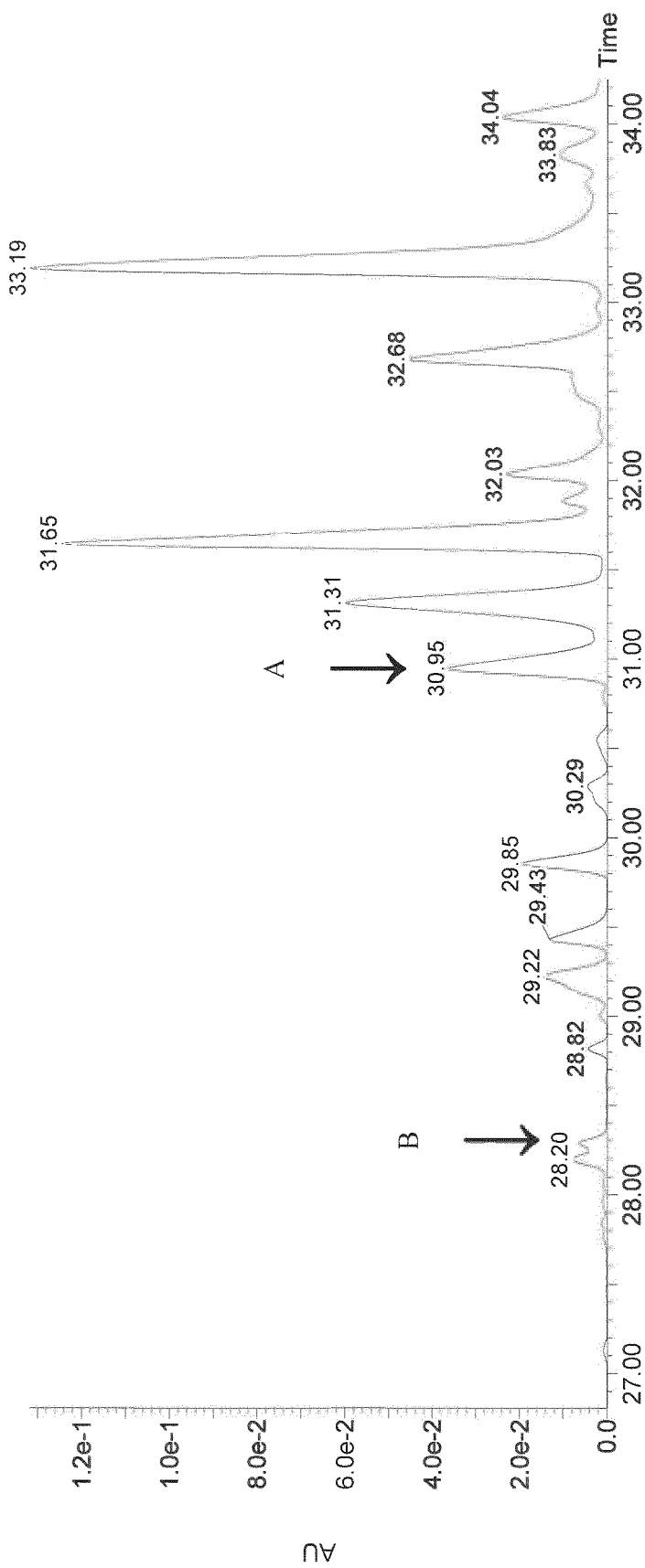
Figure 1C:
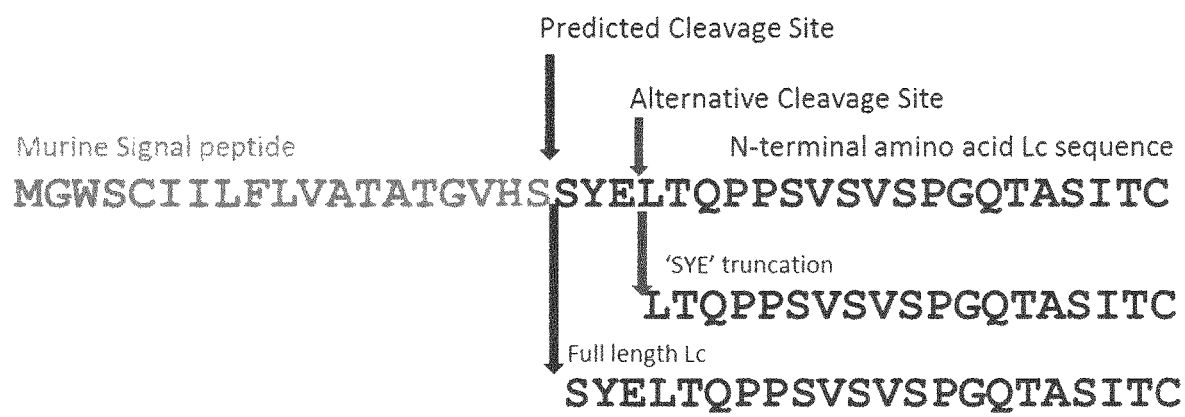

MEDI8490 was expressed with the murine Hc leader by transient transfection to support routine developability assessment studies for this molecule (Yang et al., mAbs 5:787-794, 2013). Material was produced by culturing the transfected CHO cells in CD-CHO (Life Technologies, Carlsbad, Calif.) for 13 days and harvesting the cell supernatant by centrifugation. The clarified harvest was purified by Protein A affinity chromatography using MabSelect SuRe™ (GE Healthcare Life Sciences, Piscataway, N.J.) and analyzed by reduced LC-MS (FIG. 1A). The main peak detected was consistent with the theoretical mass of the intact mAb Lc. Unusually, a lower molecular weight species consistent with a truncated Lc variant missing the first three amino acids (SYE) was also detected, and accounted for 8% of the total signal. Peptide mapping analysis confirmed the Lc truncate (FIG. 1B and FIG. 1C).

Example 3

Figure 2A:
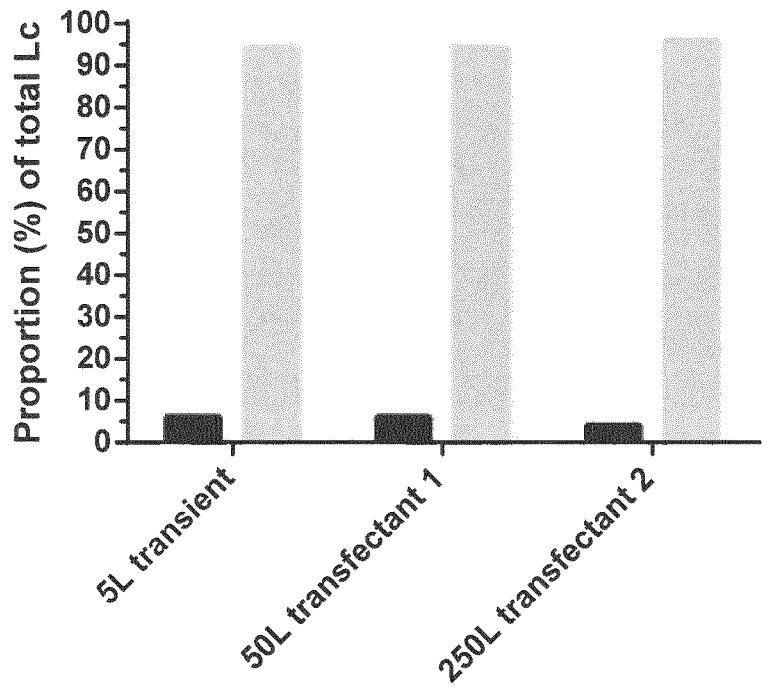
Figure 2B:
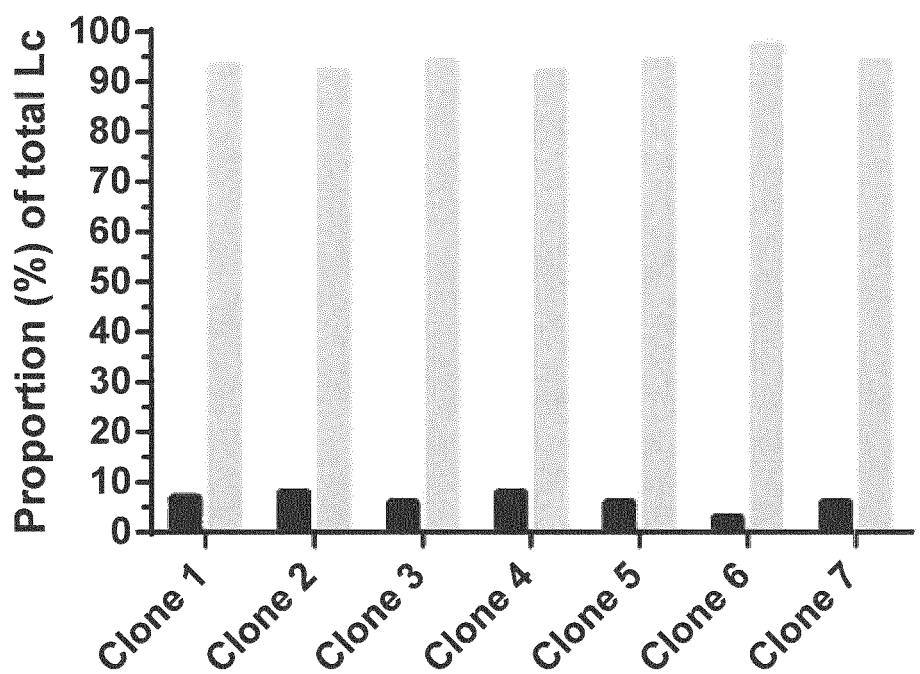
Figure 3:
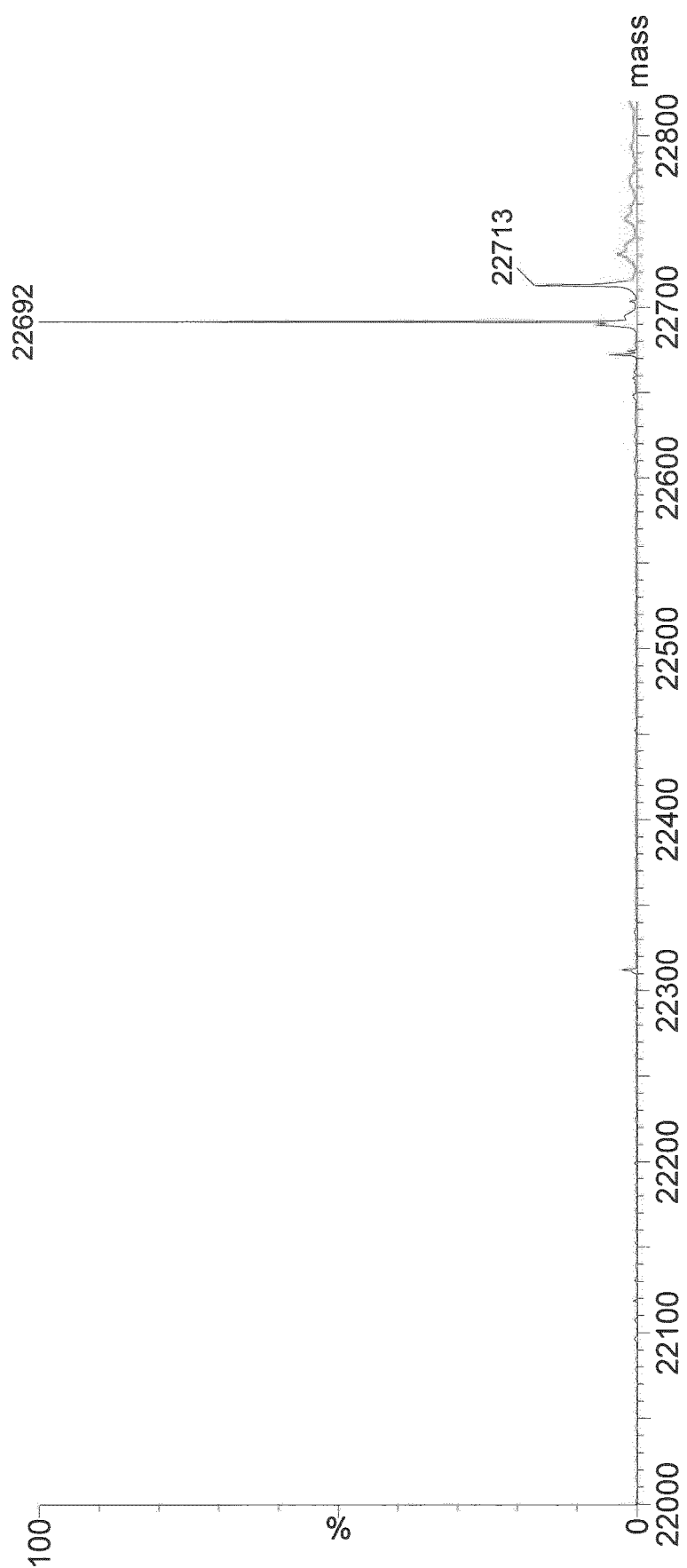
FIG. 3 shows the charge-deconvoluted mass spectrum for MEDI8490 Lc produced from an expression construct encoding the SYE Lc and the murine Hc leader sequence with its intron removed (SEQ ID NO: 5).
Figure 4:
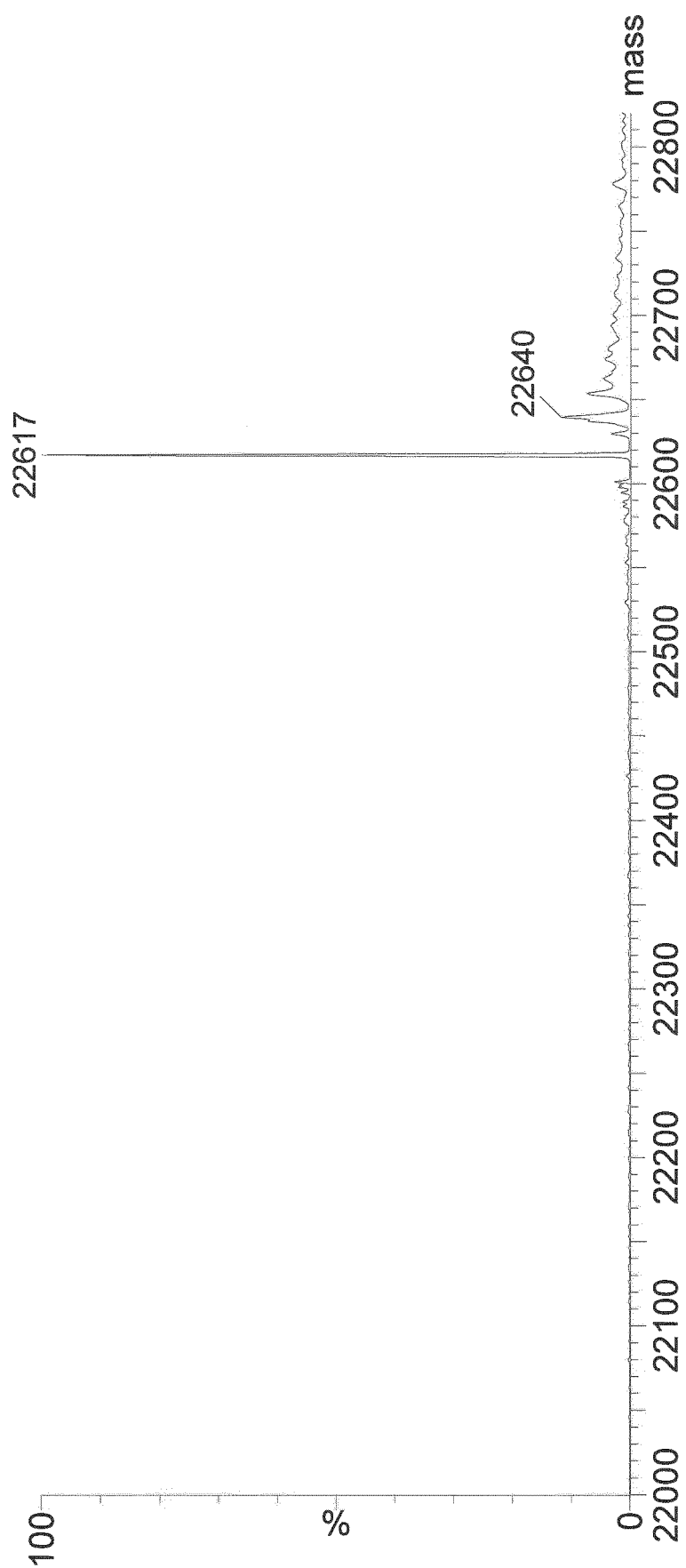
FIG. 4 shows the charge-deconvoluted mass spectrum for MEDI8490 Lc produced from an expression construct encoding the SSE Lc and the murine Hc leader sequence with its intron removed (SEQ ID NO: 6).
Figure 5:
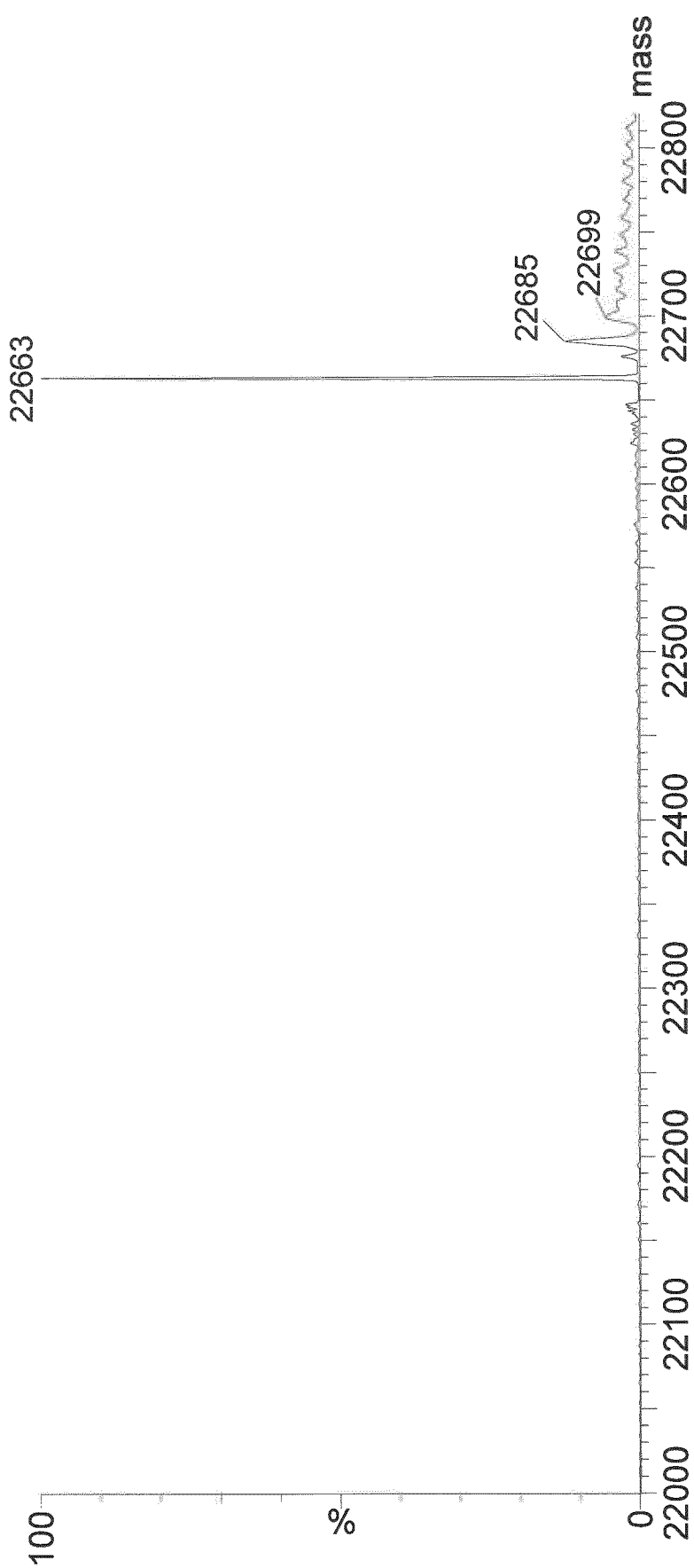
FIG. 5 shows the charge-deconvoluted mass spectrum for MEDI8490 Lc produced from an expression construct encoding the SYV Lc and the murine Hc leader sequence with its intron removed (SEQ ID NO: 7).
Figure 6:
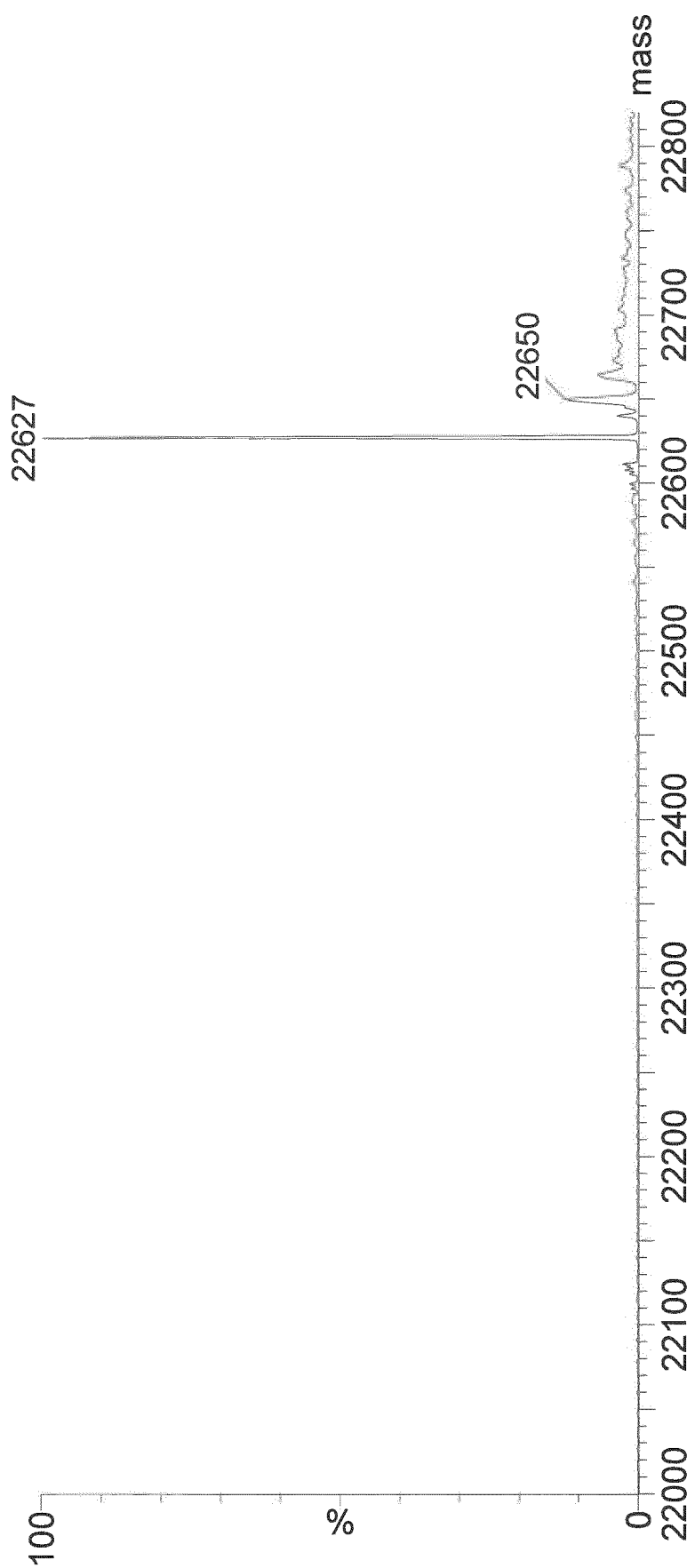
FIG. 6 shows the charge-deconvoluted mass spectrum for a MEDI8490 Lc produced from an expression construct encoding the QSV Lc and the murine Hc leader sequence with its intron removed (SEQ ID NO: 8).

Impact of Expression Platform, Cell Culture Process and Clonal Lineage on MEDI8490 Lc Truncation In order to investigate whether generation of the truncated Lc variant was process-driven, CHO cells expressing MEDI8490 from a transient tranfection at 5 L scale and two independent stable primary transfectants at 50 L and 250 L scale were run in a fed-batch process. In addition, material was generated from seven clones expressing MEDI8490, isolated from six independent stable primary transfectants at 5 L scale, to investigate the influence of clonal lineage on Lc truncation. The cell culture from all scales was harvested at day 14. MEDI8490 was purified and characterized by reduced antibody LC-MS analysis (FIG. 2A and FIG. 2B). The results show that two forms of the Lc were detected: the desired full length Lc at 92-97% and truncated Lc variant at 3-8% of the total Lc molecules. There was minimal variability in the proportion of the two Lc forms across all bioreactor scales, expression platforms and clonal lineage, demonstrating that generation of the truncated Lc variant is independent of these factors.

Example 4

Investigation of MEDI8490 Lc mRNA Processing as a Cause of Lc Truncation

The transient and stable expression plasmids for MEDI8490 contained intronic sequences within the signal peptide coding region for the Lc and Hc (Persic et al., 1997; Orlandi, 1989). To assess whether the Lc SYE truncate was transcript-encoded due to inefficient or incorrect splicing of the Lc mRNA, cDNA sequencing analysis was performed on stable clonal CHO cell lines expressing MEDI8490. RNA was isolated from four cell lines, followed by RT-PCR of the Lc mRNA and cloning of the individual resulting cDNA molecules into TOPO® vectors. Sequencing of 327 individual clones showed that the full-length light chain sequence including the N-terminal 'SYE' amino acid motif was encoded by the Lc transcripts. In addition, no alternative splice sites were identified in the MEDI8490 Lc sequence when analyzed by the GeneSplicer splice site prediction algorithm (Pertea et al., *Nucleic Acids Res.* 29:1185-1190, 2001).

Example 5

Investigation of Alternative N-Terminal Amino Acid Sequences: Using Transient Transfection We investigated whether the sequence of the N-terminus of the Lc would affect the production of the MEDI8490 Lc variant. Two alternative Lc sequences from the V-lambda 3 family, differing from the MEDI8490 Lc sequence by one amino acid at the N-terminus (SYV and SSE), were chosen for production of MEDI8490. A genetically truncated version of the MEDI8490 Lc was also constructed as a Lc truncate control in which the DNA sequence encoding the N-terminal SYE amino acids were deleted.

Transient transfections for investigating alternative N-terminal amino acid sequences were conducted. DNA sequences encoding the alternative Lc sequences with the murine Hc leader (SEQ ID NO: 1), either with or without the endogenous, native leader intron, were synthesized and cloned into the transient MEDI8490 Lc expression plasmid. Material was produced by culturing the transfected CHO cells in CD-CHO (Life Technologies, Carlsbad, Calif.) for 10-14 days in a fed-batch process and harvesting the cell supernatant by centrifugation. The clarified harvest was purified by Protein A affinity chromatography using MabSelect SuRe™ (GE Healthcare Life Sciences, Piscataway, N.J.) and characterized by QTOF mass spectrometry to detect presence/absence of the Lc truncation.

In silico analysis of each immature polypeptide containing the murine signal peptide with the alternative Lc sequences was performed using Signal P 4.1 (Petersen et al., *Nat. Methods* 8:785-786, 2011). In all cases, analysis showed that the N-terminal amino acid sequence was identified as a signal peptide and the predicted cleavage site was between position −1 and +1 (i.e. the last residue of the signal peptide and the first residue of the mature protein), indicating that the signal peptide would be cleaved leaving fully intact Lc. The results are summarized in Table 1 and representative results are shown in FIG. 1A and FIG. 3-6.

TABLE 1

| N-term. A.A. Seq. | N-term. A.A. Seq. Origin | A.A. Sequence Identifier* | Leader Intron | Truncation | Results |
|---|---|---|---|---|---|
| SYE | V-lambda 3 family | SEQ ID NO: 5 | Y | Y | FIG. 1A |
| SYE | V-lambda 3 family | SEQ ID NO: 5 | N | Y | FIG. 3 |
| SSE | V-lambda 3 family | SEQ ID NO: 6 | N | N | FIG. 4 |
| SYV | V-lambda 3 family | SEQ ID NO: 7 | N | N | FIG. 5 |
| QSV | Non-germlined sequence | SEQ ID NO: 8 | N | N | FIG. 6 |

*Sequence of leader (SEQ ID NO: 1) + N-terminal tripeptide

Lc truncate was not detected in purified material produced using any of the engineered Lc N-termini (FIG. 10B). The presence or absence of the intron in the secretory leader sequence does not affect whether the SYE truncation occurs. This indicates that the truncation is not due to transcript mis-splicing of the leader containing the intron, but that it is inherent in the leader-SYE amino acid sequence combination. No truncation occurred when the N-terminal Lc amino acid sequence was mutated to SSE, SYV, or QSV.

A genetically truncated version of the MEDI8490 Lc (ΔSYE) was also tested; this was engineered to have the SYE N-terminal deliberately removed. Thus, the Lc amino acid sequence started from the fourth amino acid in the MEDI8490 Lc sequence (SEQ ID. NO: 12). This control molecule yielded the anticipated results in that 100% of the product was truncated (FIG. 10B). It was interesting to note that we observed no further truncation of the Lc.

Example 6

Investigation of Alternative Leader Sequences Using Transient Transfection

Transient transfections for investigating alternative leader sequences were conducted using the 'SYE' N-terminal amino acid start sequence for the Lc. Three different naturally occurring human signal peptides from the V-lambda 1, V-lambda 3 and V-kappa 1 families were chosen for analysis alongside the murine signal peptide. Material was produced and analyzed using the methods described above except that all Lc sequences contained the 'SYE' N-terminal motif, and the leader sequences were varied, as shown in Table 2. With the exception of the murine reference standard, all leader sequences were cDNA format (i.e. they did not contain an intron), as the presence or absence of the intron had previously been shown to be irrelevant to the production of truncated material. As described above, analysis showed that the N-terminal amino acid sequence was identified as a signal peptide and the predicted cleavage site was between position −1 and +1 (i.e. the last residue of the signal peptide and the first residue of the mature protein), indicating that the signal peptide would be cleaved leaving fully intact Lc. No truncation of the Lc was observed when alternative leader sequences from the V-lambda 3, V-lambda 1 or V-kappa 1 families were used.

TABLE 2

Figure 7:
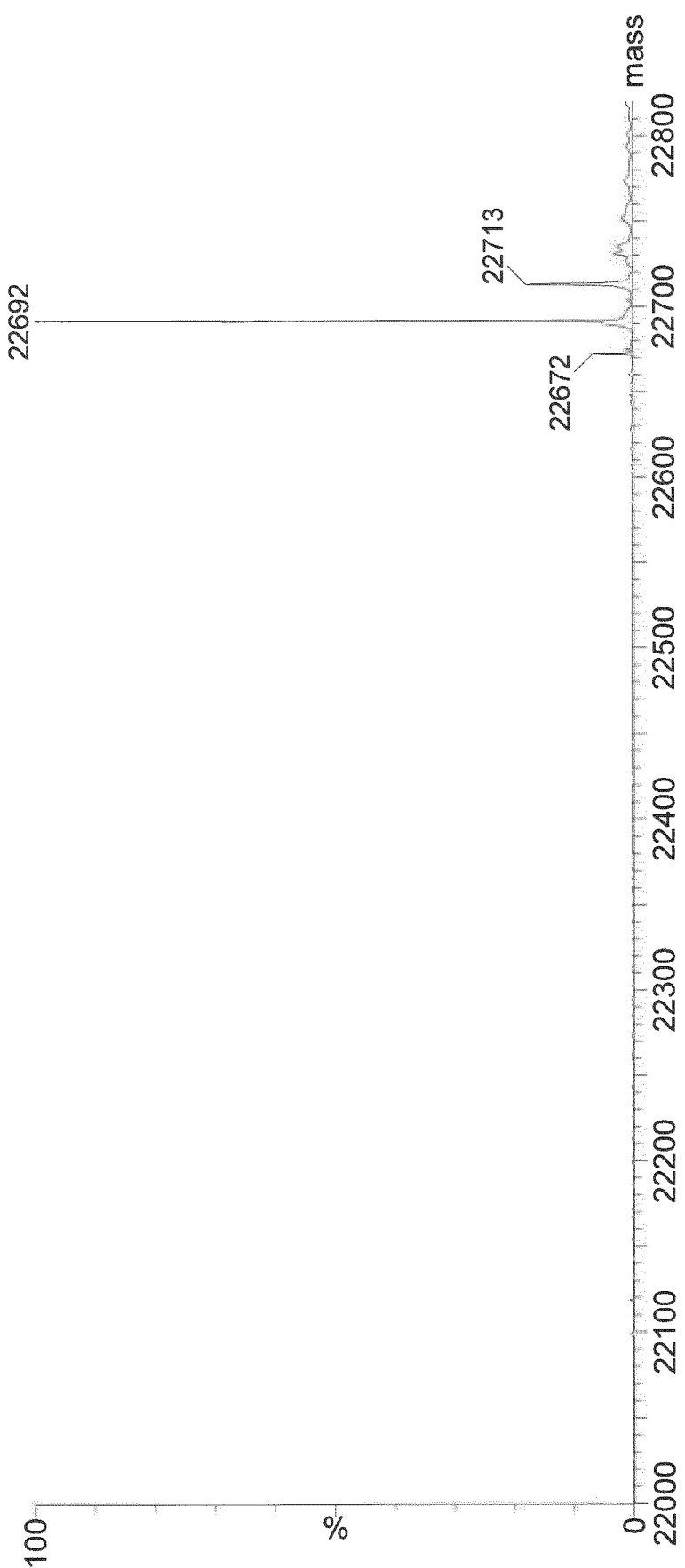
FIG. 7 shows the charge-deconvoluted mass spectrum for a MEDI8490 Lc produced from an expression construct encoding the SYE Lc and the V-lambda 3 leader sequence with its intron removed (SEQ ID NO: 12).
Figure 8:
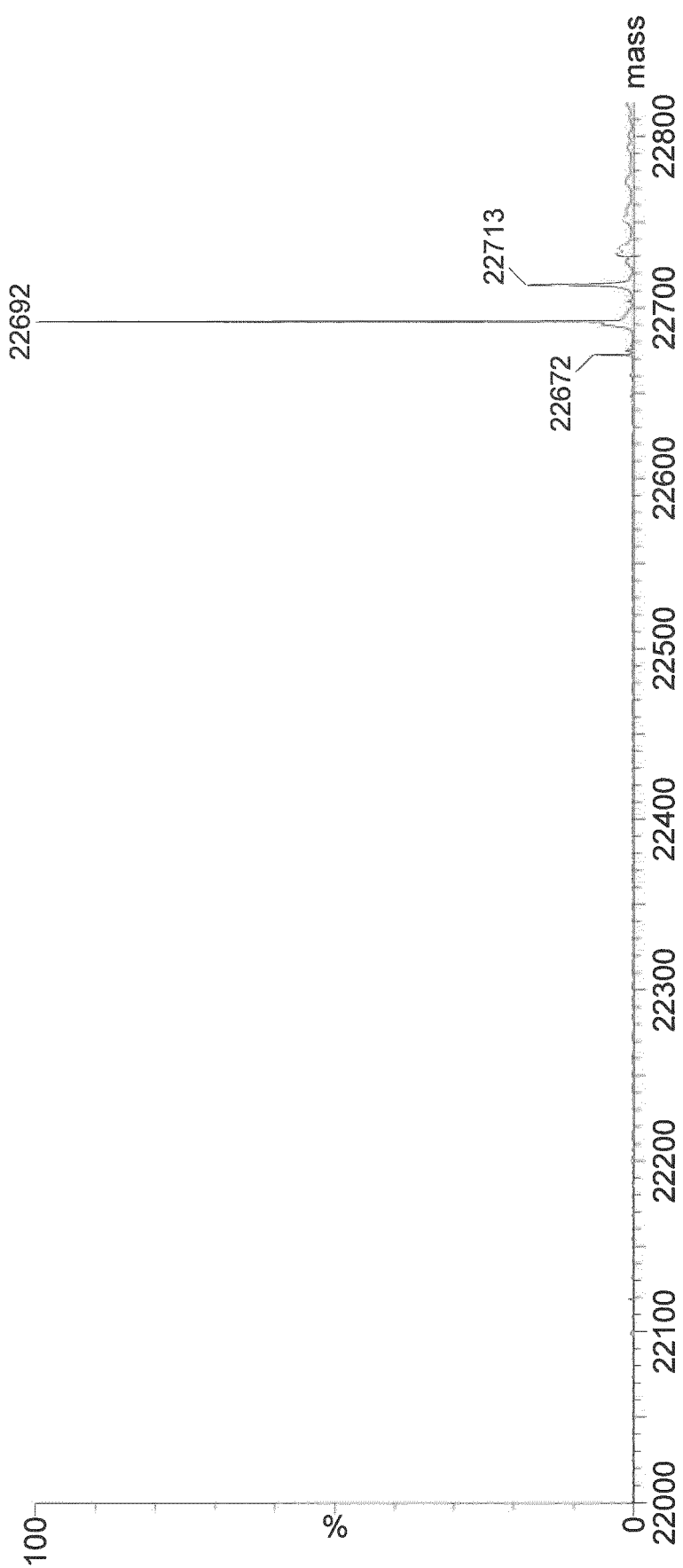
FIG. 8 shows the charge-deconvoluted mass spectrum for a MEDI8490 Lc produced from an expression construct encoding the SYE Lc and the V-lambda 1 leader sequence with its intron removed (SEQ ID NO: 13).
Figure 9:
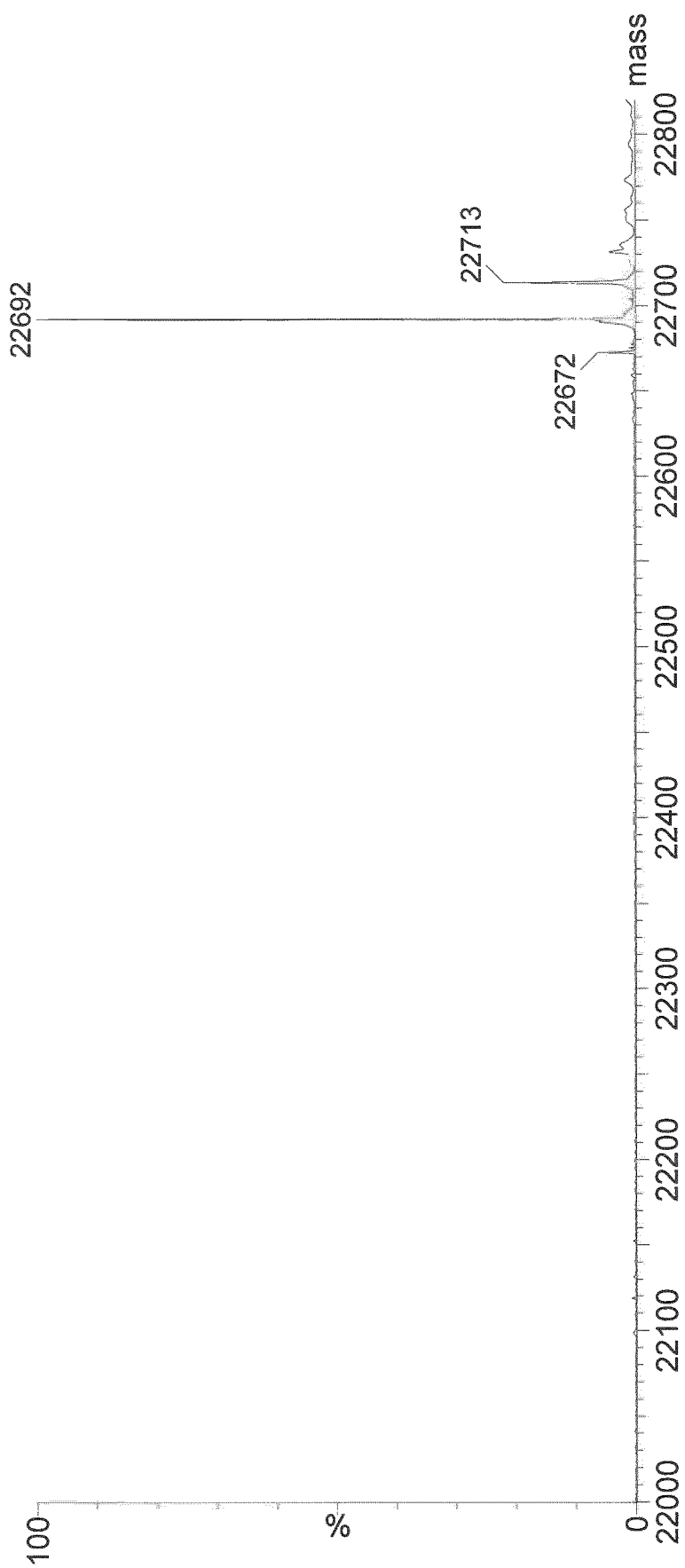
FIG. 9 shows the charge-deconvoluted mass spectrum for a MEDI8490 Lc produced from an expression construct encoding the SYE Lc and the kappa leader sequence with its intron removed (SEQ ID NO: 14).

| Leader Sequence | Leader Sequence Origin | A.A. Sequence Identifier* | Truncation | Results |
|---|---|---|---|---|
| MGWSCIILFLV ATATGVHS | Murine (w/intron) | SEQ ID NO: 5 | Y | FIG. 1A |
| MGWSCIILFLV ATATGVHS | Murine (w/o intron) | SEQ ID NO: 5 | Y | FIG. 3 |
| MAWTPLLLPLL TFCTVSEA | V-lambda 3 family | SEQ ID NO: 12 | N | FIG. 6 |
| MAGFPLLLTLL THCAGSWA | V-lambda 1 family | SEQ ID NO: 13 | N | FIG. 7 |
| MDMRVPAQLLG LLLLWLPGAKC | V-kappa 1 family | SEQ ID NO: 14 | N | FIG. 8 |

*Sequence of leader + N-terminal tripeptide

LC-MS analysis of purified MEDI8490 samples revealed intact Lc as the predominant species, measured between 93-96% of the Lc molecules. Low levels of the SYE Lc truncate at 4% and 7% were only detected in material produced using the murine signal peptide with (Sig 1) or without (Sig 2) the naturally occurring intron (FIG. 10A). The levels of SYE truncate were consistent with earlier results (FIG. 1A) and the presence or absence of the intron in the murine signal peptide sequence did not impact the presence of the SYE truncate. Lc truncate was not detected in purified material produced using any of the alternative signal peptides (FIG. 10A). These data further indicate that the truncation is not due to mis-splicing of the leader containing the intron but that it is inherent in the murine signal peptide-SYE amino acid combination.

Example 7

Investigation of Alternative N-Terminal Light Chain Amino Acid Sequences and Alternative Leader Sequences Using Stable Transfection The examples described above show that either altering the N-terminal amino acid sequence of the Lc or changing the secretory leader peptide sequence is successful in preventing 'SYE' truncation of Lc peptides in transient transfection. Stably transfected CHO pools were also investigated. The murine and alternative leaders were both codon-optimized in the presence of the variable Lc sequence and were used to construct plasmids with the MEDI8490 heavy and light chain genes, both incorporated onto the same plasmid, with a selectable marker for stable cell line selection. The leaders were in cDNA format (i.e. no intron). The antibody material was accumulated using a fed-batch process. MEDI8490 was purified and analyzed for the presence of Lc truncate by LC-MS (FIG. 10A). For the material produced using the murine signal peptide, the mass spectra data identified a minor peak at 5% and 7% of the total Lc molecules for pool 1 and pool 2, respectively and was attributed to SYE Lc truncate. In contrast, the SYE Lc truncate was not detected in the material produced using the human V-lambda 1 signal peptide. Thus, the stable pools showed that the expression predicted by the transiently transfected material is confirmed in stable cell lines (Table 3).

TABLE 3

| Leader Origin | Leader Sequence | N-term. A.A. Seq. | A.A. Sequence Identifier* | Truncated |
|---|---|---|---|---|
| Murine leader (codon optimized) | MGWSCIILFL VATATGVHS | SYE | SEQ ID NO: 5 | Y |
| V-lambda 1 leader (codon optimized) | MAGFPLLLTL LTHCAGSWA | SYE | SEQ ID NO: 13 | N |

*Sequence of leader + N-terminal tripeptide

Example 8

Effect of Signal Peptide on Lc Truncation in Alternative mAbs with SYE Lcs

To investigate whether the production and prevention of Lc truncation was unique to MEDI8490, we assessed the murine (Sig. 1; SEQ ID NO: 1) and human V-lambda 1 (Sig. 4; SEQ ID NO: 3) signal peptides with two unrelated monoclonal antibodies, mAb A and mAb B, which have an SYE Lc N-terminal motif. The DNA sequences encoding the signal peptides were synthesized and cloned into transient mAb A and mAb B Lc expression plasmids. Each resulting Lc expression plasmid, along with the corresponding Hc expression plasmid, was used to transiently transfect CHO cells. The clarified fed-batch harvests were purified by Protein A affinity chromatography. Analysis by LC-MS (FIG. 10C) revealed the presence of Lc truncate in mAb A and mAb B when the murine signal peptide was used, but absent when the human V-lambda 1 signal peptide was used. The results are summarized in Table 4.

TABLE 4

| Molecule | Leader sequence | N-term. A.A. Seq. | A.A. Sequence Identifier* | Truncate detected (Y/N) |
|---|---|---|---|---|
| mAb A | MGWSCIILFL VATATGVHS (Sig. 1) | SYE | SEQ ID NO: 5 | Y |
| mAb A | MAGFPLLLTL LTHCAGSWA (Sig. 4) | SYE | SEQ ID NO: 13 | N |
| mAb B | MGWSCIILFL VATATGVHS (Sig. 1) | SYE | SEQ ID NO: 5 | Y |
| mAb B | MAGFPLLLTL LTHCAGSWA (Sig. 4) | SYE | SEQ ID NO: 13 | N |

*Sequence of leader + N-terminal tripeptide

These data show that the production of Lc truncate is not unique to MEDI8490 and can occur with other mAbs where the Lc has an N-terminal SYE amino acid motif. Furthermore, similar to MEDI8490, the production of the SYE truncate can be prevented in other mAbs by using an alternative to the murine signal peptide.

SEQUENCES

Table 5 shows a listing of amino acid and nucleotide sequences used herein.

TABLE 5

| Sequence Identifier | Sequence | Description |
|---|---|---|
| 1 | MGWSCIILFLVATATGVHS | A.A. seq. of murine leader w/intron: Sig. 1 w/out intron: Sig. 2 |
| 2 | MAWTPLLLPLLTFCTSEA | A.A. seq. of V-lambda 3 leader: Sig. 3 |
| 3 | MAGFPLLLTLLTHCAGSWA | A.A. seq. of V-lambda 1 leader: Sig. 4 |
| 4 | MDMRVPAQLLGLLLLWLPGAKC | A.A. seq. of V-kappa 1 leader: Sig. 5 |
| 5 | MGWSCIILFLVATATGVHS*SYE* | A.A. seq. of murine leader + original V-lambda 3 N-terminal tripeptide |
| 6 | MGWSCIILFLVATATGVHS*SSE* | A.A. seq. of murine leader + alternate V-lambda 3 N-terminal tripeptide |
| 7 | MGWSCIILFLVATATGVHS*SYV* | A.A. seq. of murine leader + alternate V-lambda 3 N-terminal tripeptide |
| 8 | MGWSCIILFLVATATGVHS*QSV* | A.A. seq. of murine leader + non-germlined N-terminal tripeptide |
| 9 | MGWSCIILFLVATATGVHS*QAV* | A.A. seq. of murine leader + alternate N-terminal tripeptide |
| 10 | MGWSCIILFLVATATGVHS*QSA* | A.A. seq. of murine leader + alternate N-terminal tripeptide |
| 11 | MGWSCIILFLVATATGVHS*QYV* | A.A. seq. of murine leader + alternate N-terminal tripeptide |
| 12 | MAWTPLLLPLLTFCTSEA*SYE* | A.A. seq. of V-lambda 3 leader + original IGLV3 N-terminal tripeptide |
| 13 | MAGFPLLLTLLTHCAGSWA*SYE* | A.A. seq. of V-lambda 1 leader + original IGLV3 N-terminal tripeptide |
| 14 | MDMRVPAQLLGLLLLWLPGAKC*SYE* | A.A. seq. of V-kappa 1 leader + original V-lambda 3 N-terminal tripeptide |
| 15 | *SYE*LTQPPSVSVSPGQTASITCSGHNLEDKFASWYQQKPGQSPVLVIYRDDKRPSGIPERFSASNSGHTATLTISGTQAMDEADYYCQAQDSTTRVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS | A.A. seq. of MEDI8490 SYE Lc |

TABLE 5-continued

| Sequence Identifier | Sequence | Description |
|---|---|---|
| 16 | ATGGGATGGAGCTGTATCATCCTCT TCTTGGTAGCAACAGCTACAGgtaa ggggttaacagtagcaggcttgagg tctggacatatatatgggtgacaat gacatccactttgcctttctctcca cagGCGTGCACTC | Nucleotide seq. of murine leader w/out intron |
| 17 | ATGGGATGGAGCTGTATCATCCTCT TCTTGGTAGCAACAGCTAcaggtaa ggggttaacagtagcaggcttgagg tctggacatatatatgggtgacaat gacatccactttgcctttctctcca cAGGCGTGCACTC | Nucleotide seq. of murine leader w/intron in lower case |
| 18 | ATGGCCTGGACCCCCCTGCTGCTGC CCCTGCTGACCTTCTGCACCGTGTC CGAGGCC | Nucleotide seq. of V-lambda 3 leader |
| 19 | ATGGCCGGCTTCCCCCTGCTGCTGA CCCTGCTGACACACTGTGCCGGCAG CTGGGCC | Nucleotide seq. of V-lambda 1 leader |
| 20 | ATGGACATGAGGGTGCCCGCCCAGC TGCTGGGCCTGCTGCTGCTGTGGCT GCCCGGGGCCAAGTGC | Nucleotide seq. of V-kappa 1 leader |
| 21 | SYELTQPPSVSVSPGQTASITCSGH NLEDK | A.A. seq. of intact N-term. tryptic peptide |
| 22 | LTQPPSVSVSPGQTASITCSGHNLE DK | A.A. seq. of truncated N-term. tryptic peptide |

The foregoing description of the specific embodiments will fully reveal the general nature of the invention such that others can, without undue experimentation, apply knowledge that is within the ordinary skill of those in the art to readily modify and/or adapt such specific embodiments for various applications without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance. The present invention is further described by the following claims.

The invention claimed is:

1. A method of producing an untruncated mature antibody light chain (Lc) polypeptide, the method comprising:
    a. identifying a first antibody Lc amino acid sequence comprising a first nascent N-terminal sequence shown in SEQ ID NO: 5; and
    b. expressing in a cultured cell a second antibody Lc polypeptide having the same amino acid sequence as the first antibody Lc polypeptide, except that instead of the first nascent N-terminal sequence, the second antibody Lc polypeptide comprises a second nascent N-terminal sequence selected from the group consisting of:
    SEQ ID NO: 6,
    SEQ ID NO: 7,
    SEQ ID NO: 8,
    SEQ ID NO: 9,
    SEQ ID NO: 10,
    SEQ ID NO: 11,
    SEQ ID NO: 12,
    SEQ ID NO: 13; and
    SEQ ID NO: 14
thereby producing an untruncated mature antibody Lc polypeptide.

2. A method of preventing N-terminal truncation of an antibody light chain (Lc) polypeptide, the method comprising:
    a. identifying a first antibody Lc polypeptide having an amino acid sequence comprising a first nascent N-terminal sequence shown in SEQ ID NO: 5, wherein the first nascent N-terminal sequence consists essentially of a leader sequence and a mature N-terminal tripeptide, wherein the mature N-terminal tripeptide is selected from the group consisting of SYE, SSE, SYV, QSV, QAV, QSA, QYV;
    wherein expression of the first antibody Lc polypeptide in a cultured cell results in truncation of the mature N-terminal tripeptide in at least about 3% of first antibody Lc polypeptides expressed in the cultured cell; and
    b. expressing in a cultured cell a second antibody Lc polypeptide having the same amino acid sequence as the first antibody Lc polypeptide, except that instead of the first nascent N-terminal sequence, the second antibody Lc polypeptide comprises a second nascent N-terminal sequence selected from the group consisting of:
    SEQ ID NO: 6,
    SEQ ID NO: 7,
    SEQ ID NO: 8,
    SEQ ID NO: 9,
    SEQ ID NO: 10,
    SEQ ID NO: 11,
    SEQ ID NO: 12,
    SEQ ID NO: 13, and
    SEQ ID NO: 14;
    wherein the second nascent N-terminal sequence consists essentially of a leader sequence and a mature N-terminal tripeptide, wherein the mature N-terminal tripeptide is selected from the group consisting of SYE, SSE, SYV, QSV, QAV, QSA, QYV; and wherein expression of the second antibody Lc polypeptide in the cultured cell results in no truncation of the mature N-terminal tripeptide; thereby preventing N-terminal truncation of an antibody Lc polypeptide.

3. A method of producing a composition comprising a homogenous population of antibody light chain (Lc) polypeptides, the method comprising:
    a. identifying a first Lc polypeptide having an amino acid sequence comprising a first nascent N-terminal sequence shown in SEQ ID NO: 5;
    b. expressing in a cultured cell a second Lc polypeptide, wherein the second Lc polypeptide has the same amino acid sequence as the first Lc polypeptide, except that the second Lc polypeptide comprises a second nascent N-terminal sequence selected from the group consisting of:
SEQ ID NO: 6,
SEQ ID NO: 7,
SEQ ID NO: 8,
SEQ ID NO: 9,
SEQ ID NO: 10,
SEQ ID NO: 11,
SEQ ID NO: 12,
SEQ ID NO: 13, and
SEQ ID NO: 14;
  wherein the second Lc polypeptide is secreted into supernatant by the cultured cell, wherein the supernatant is at least 98% free of amino acid sequence variants of the second Lc polypeptide; and
  c. harvesting the second Lc polypeptide from the supernatant;
  thereby producing a composition comprising a homogenous population of antibody Lc polypeptides.

4. The method according to claim 1 wherein the second nascent N-terminal sequence is SEQ ID NO: 6.

5. The method according to claim 1, wherein the second nascent N-terminal sequence is SEQ ID NO: 7.

6. The method according to claim 1, wherein the second nascent N-terminal sequence is SEQ ID NO: 8.

7. The method according to claim 1, wherein the second nascent N-terminal sequence is SEQ ID NO: 9.

8. The method according to claim 1, wherein the second nascent N-terminal sequence is SEQ ID NO: 10.

9. The method according to claim 1, wherein the second nascent N-terminal sequence is SEQ ID NO: 11.

10. The method according to claim 1, wherein the second nascent N-terminal sequence is SEQ ID NO: 12.

11. The method according to claim 1, wherein the second nascent N-terminal sequence is SEQ ID NO: 13.

12. The method according to claim 1, wherein the second nascent N-terminal sequence is SEQ ID NO: 14.

13. The method according to claim 1, wherein the cultured cell is a Chinese hamster ovary (CHO) cell.

14. The method according to claim 1, wherein N-terminal truncation is detected by liquid chromatography-mass spectrometry (LC-MS) analysis.

15. The method according to claim 14, wherein N-terminal truncation is confirmed by reduced peptide mapping analysis.

16. The method according to claim 3, wherein the percentages of the second Lc polypeptide and the amino acid sequence variants in the supernatant is determined by LC-MS analysis.

17. The method according to claim 3, wherein the supernatant is at least 99% free of amino acid sequence variants of the second Lc polypeptide.

18. The method according to claim 3, wherein the supernatant is 100% free of amino acid sequence variants of the second Lc polypeptide.

19. The method according to claim 3, wherein the composition is a pharmaceutical composition.

20. The method according to claim 3, wherein the first Lc polypeptide is part of an antibody.

21. The method according to claim 3, wherein the second Lc polypeptide is part of an antibody.

22. The method according to claim 21, wherein the antibody is a therapeutic antibody.

* * * * *

SEQUENCE LISTING

```
<160> NUMBER OF SEQ ID NOS: 26

<210> SEQ ID NO 1
<211> LENGTH: 19
<212> TYPE: PRT
<213> ORGANISM: Mus sp.

<400> SEQUENCE: 1

Met Gly Trp Ser Cys Ile Ile Leu Phe Leu Val Ala Thr Ala Thr Gly
1               5                   10                  15

Val His Ser

<210> SEQ ID NO 2
<211> LENGTH: 18
<212> TYPE: PRT
<213> ORGANISM: Homo sapiens

<400> SEQUENCE: 2

Met Ala Trp Thr Pro Leu Leu Leu Pro Leu Leu Thr Phe Cys Thr Ser
1               5                   10                  15

Glu Ala
```

```
<210> SEQ ID NO 3
<211> LENGTH: 19
<212> TYPE: PRT
<213> ORGANISM: Homo sapiens

<400> SEQUENCE: 3

Met Ala Gly Phe Pro Leu Leu Leu Thr Leu Leu Thr His Cys Ala Gly
1               5                   10                  15

Ser Trp Ala

<210> SEQ ID NO 4
<211> LENGTH: 22
<212> TYPE: PRT
<213> ORGANISM: Homo sapiens

<400> SEQUENCE: 4

Met Asp Met Arg Val Pro Ala Gln Leu Leu Gly Leu Leu Leu Leu Trp
1               5                   10                  15

Leu Pro Gly Ala Lys Cys
            20

<210> SEQ ID NO 5
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Met Gly Trp Ser Cys Ile Ile Leu Phe Leu Val Ala Thr Ala Thr Gly
1               5                   10                  15

Val His Ser Ser Tyr Glu
            20

<210> SEQ ID NO 6
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Met Gly Trp Ser Cys Ile Ile Leu Phe Leu Val Ala Thr Ala Thr Gly
1               5                   10                  15

Val His Ser Ser Ser Glu
            20

<210> SEQ ID NO 7
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Met Gly Trp Ser Cys Ile Ile Leu Phe Leu Val Ala Thr Ala Thr Gly
1               5                   10                  15

Val His Ser Ser Tyr Val
            20
```

```
<210> SEQ ID NO 8
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Met Gly Trp Ser Cys Ile Ile Leu Phe Leu Val Ala Thr Ala Thr Gly
1               5                   10                  15

Val His Ser Gln Ser Val
            20

<210> SEQ ID NO 9
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Met Gly Trp Ser Cys Ile Ile Leu Phe Leu Val Ala Thr Ala Thr Gly
1               5                   10                  15

Val His Ser Gln Ala Val
            20

<210> SEQ ID NO 10
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Met Gly Trp Ser Cys Ile Ile Leu Phe Leu Val Ala Thr Ala Thr Gly
1               5                   10                  15

Val His Ser Gln Ser Ala
            20

<210> SEQ ID NO 11
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Met Gly Trp Ser Cys Ile Ile Leu Phe Leu Val Ala Thr Ala Thr Gly
1               5                   10                  15

Val His Ser Gln Tyr Val
            20

<210> SEQ ID NO 12
<211> LENGTH: 21
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 12

Met Ala Trp Thr Pro Leu Leu Leu Pro Leu Thr Phe Cys Thr Ser
1               5                   10                  15

Glu Ala Ser Tyr Glu
            20

<210> SEQ ID NO 13
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Met Ala Gly Phe Pro Leu Leu Leu Thr Leu Leu Thr His Cys Ala Gly
1               5                   10                  15

Ser Trp Ala Ser Tyr Glu
            20

<210> SEQ ID NO 14
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Met Asp Met Arg Val Pro Ala Gln Leu Leu Gly Leu Leu Leu Leu Trp
1               5                   10                  15

Leu Pro Gly Ala Lys Cys Ser Tyr Glu
            20                  25

<210> SEQ ID NO 15
<211> LENGTH: 212
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Ser Tyr Glu Leu Thr Gln Pro Pro Ser Val Ser Val Ser Pro Gly Gln
1               5                   10                  15

Thr Ala Ser Ile Thr Cys Ser Gly His Asn Leu Glu Asp Lys Phe Ala
                20                  25                  30

Ser Trp Tyr Gln Gln Lys Pro Gly Gln Ser Pro Val Leu Val Ile Tyr
            35                  40                  45

Arg Asp Asp Lys Arg Pro Ser Gly Ile Pro Glu Arg Phe Ser Ala Ser
        50                  55                  60

Asn Ser Gly His Thr Ala Thr Leu Thr Ile Ser Gly Thr Gln Ala Met
65                  70                  75                  80

Asp Glu Ala Asp Tyr Tyr Cys Gln Ala Gln Asp Ser Thr Thr Arg Val
                85                  90                  95
```

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 16
<211> LENGTH: 138
<212> TYPE: DNA
<213> ORGANISM: Mus sp.

<400> SEQUENCE: 16
atgggatgga gctgtatcat cctcttcttg gtagcaacag ctacaggtaa ggggttaaca      60
gtagcaggct tgaggtctgg acatatatat gggtgacaat gacatccact ttgcctttct     120
ctccacaggc gtgcactc                                                    138

<210> SEQ ID NO 17
<211> LENGTH: 138
<212> TYPE: DNA
<213> ORGANISM: Mus sp.

<400> SEQUENCE: 17
atgggatgga gctgtatcat cctcttcttg gtagcaacag ctacaggtaa ggggttaaca      60
gtagcaggct tgaggtctgg acatatatat gggtgacaat gacatccact ttgcctttct     120
ctccacaggc gtgcactc                                                    138

<210> SEQ ID NO 18
<211> LENGTH: 57
<212> TYPE: DNA
<213> ORGANISM: Homo sapiens

<400> SEQUENCE: 18
atggcctgga ccccctgct gctgcccctg ctgaccttct gcaccgtgtc cgaggcc          57

<210> SEQ ID NO 19
<211> LENGTH: 57
<212> TYPE: DNA
<213> ORGANISM: Homo sapiens

<400> SEQUENCE: 19
atggccggct tccccctgct gctgaccctg ctgacacact gtgccggcag ctgggcc         57

<210> SEQ ID NO 20
<211> LENGTH: 66
<212> TYPE: DNA
<213> ORGANISM: Homo sapiens

<400> SEQUENCE: 20
atggacatga gggtgcccgc ccagctgctg ggcctgctgc tgctgtggct gcccggggcc    60
aagtgc    66

<210> SEQ ID NO 21
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Ser Tyr Glu Leu Thr Gln Pro Pro Ser Val Ser Val Ser Pro Gly Gln
1               5                   10                  15

Thr Ala Ser Ile Thr Cys Ser Gly His Asn Leu Glu Asp Lys
            20                  25                  30

<210> SEQ ID NO 22
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Leu Thr Gln Pro Pro Ser Val Ser Val Ser Pro Gly Gln Thr Ala Ser
1               5                   10                  15

Ile Thr Cys Ser Gly His Asn Leu Glu Asp Lys
            20                  25

<210> SEQ ID NO 23
<211> LENGTH: 19
<212> TYPE: PRT
<213> ORGANISM: Homo sapiens

<400> SEQUENCE: 23

Met Ala Trp Thr Pro Leu Leu Leu Pro Leu Leu Thr Phe Cys Thr Val
1               5                   10                  15

Ser Glu Ala

<210> SEQ ID NO 24
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Met Gly Trp Ser Cys Ile Ile Leu Phe Leu Val Ala Thr Ala Thr Gly
1               5                   10                  15

Val His Ser Ser Tyr Glu Leu Thr Gln Pro Pro Ser Val Ser Val Ser
            20                  25                  30

Pro Gly Gln Thr Ala Ser Ile Thr Cys
            35                  40

```
<210> SEQ ID NO 25
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Leu Thr Gln Pro Pro Ser Val Ser Val Ser Pro Gly Gln Thr Ala Ser
1               5                   10                  15

Ile Thr Cys

<210> SEQ ID NO 26
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Ser Tyr Glu Leu Thr Gln Pro Pro Ser Val Ser Val Ser Pro Gly Gln
1               5                   10                  15

Thr Ala Ser Ile Thr Cys
            20
```